United States Patent [19]

Clark

[11] Patent Number: 4,844,063
[45] Date of Patent: Jul. 4, 1989

[54] SURGICAL DIATHERMY APPARATUS

[76] Inventor: Ronald D. Clark, 54 Woodbank Crescent, Clarkston, Glasgow G76 7DR, United Kingdom

[21] Appl. No.: 101,562

[22] Filed: Sep. 28, 1987

[30] Foreign Application Priority Data

Sep. 27, 1986 [GB] United Kingdom ............... 8623293
Nov. 14, 1986 [GB] United Kingdom ............... 8627282

[51] Int. Cl.⁴ ............................................. A61B 17/39
[52] U.S. Cl. ............................................. 128/303.13
[58] Field of Search .................. 128/303.13, 303.14, 128/303.17

[56] References Cited

U.S. PATENT DOCUMENTS 4,188,927 2/1980 Harris ........................ 128/303.14
4,200,104 4/1980 Harris ........................ 128/303.14

FOREIGN PATENT DOCUMENTS 2516782 11/1981 France ........................ 128/303.13

Primary Examiner—Lee S. Cohen
Attorney, Agent, or Firm—Ratner & Prestia

[57] ABSTRACT

A surgical diathermy apparatus which virtually eliminates the possibility of burns to the patient from faulty return current electrodes applied to the skin, and other causes. A capacitive neutral plate system is employed as return electrodes, along with injection of a compensating potential in series opposition to the potential drop across the capacitive neutral plate system. The apparatus can also incorporate testing, measuring, alarm, and safety cut-off systems. The invention can be applied to completely new diathermy apparatus, or as a retrofit improvement to existing equipment.

10 Claims, 20 Drawing Sheets

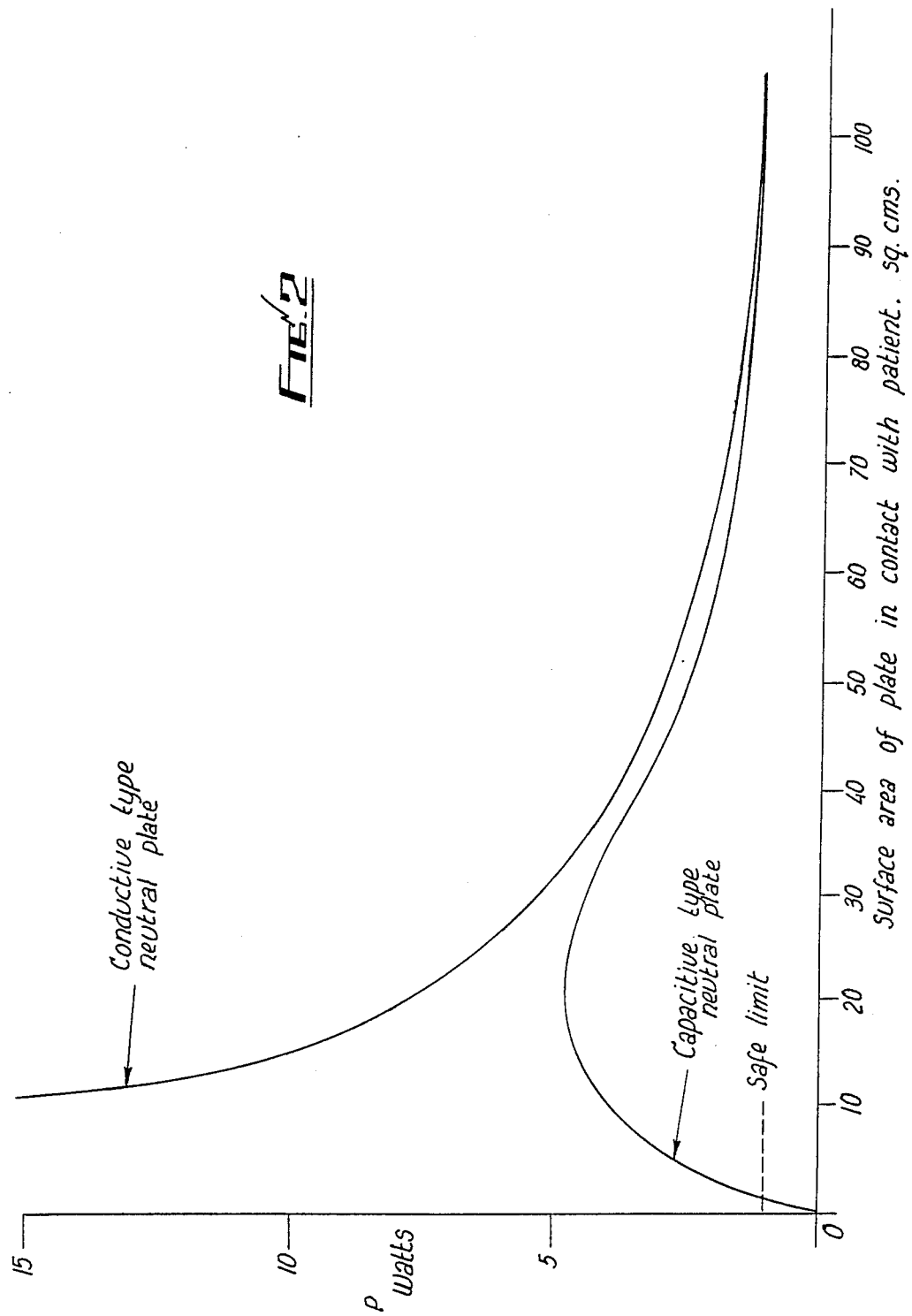

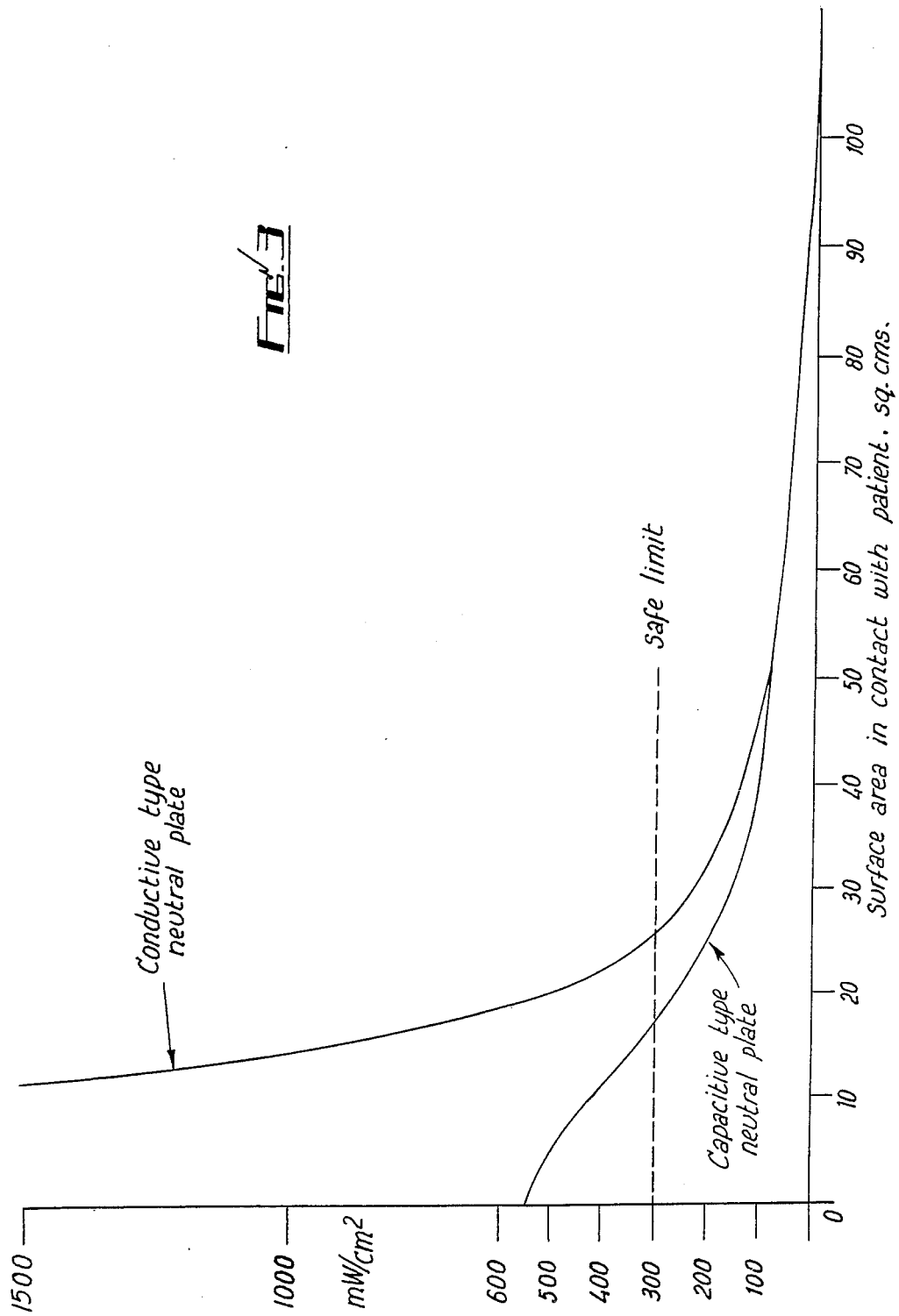

SURGICAL DIATHERMY APPARATUS

This invention relates to surgical diathermy apparatus using indifference plates of the capacitance coupling type.

BACKGROUND OF THE INVENTION

1. Surgical Diathermy and the Indifference Plate

Surgical diathermy is an electrical method of producing cuts in human tissue. This is done by striking an electric arc by a stylus which completes an electric circuit through the human body. A typical frequency of operation is 600 kHz and the range of power outputs from a diathermy set varies from a few Watts to about 400 W. A diagrammatic view of a typical arrangement is shown in FIG. 1, where:

$Z1$ represents the contact impedance between the active electrode and the patient, say 400 ohm, mainly resistive;

$Z2$ represents the impedance of the current path within the patient's body, typically 20 ohm, mainly resistive;

$Z3$ represents the contact impedance between the plate electrode and the patient, typically 2 ohm, mainly resistive; and $Z4$ represents the impedance of the plate cable, typically 30 ohm, mainly inductive.

The return path of the electric current is conveyed from the human body to the diathermy machine by a metal plate of sufficient area that the current density is harmlessly low. This is called the "neutral plate", "indifference plate" or simply "plate electrode".

The indifference plate has undergone some development. Initial types were of lead sheet bound to the patient by dressings and with saline solution added to give good electrical conductivity. Modern types are of foil, the more recent types having an adhesive conductive film which gives good electrical contact with the patient and high security of fixing. The claimed contact impedance of one example of this adhesive type is 15 ohms.

2. The Capacitive Type of Indifference Plate

An alternative approach, which also claims an improved current distribution over former types is the capacitive type. This also is a foil type with an adhesive layer. This adhesive, however, is not conductive but an insulator, so that the return circuit is made through a capacitive reactance. A measured value of the reactance of a commercial plate of this type when attached to a stiff aluminium plate was found to be around 30 ohms. This is twice the contact impedance of the above-mentioned conductive plate and 15 times that of a typical plate electrode of FIG. 1. Some crude measurements of the impedance of a capacitive type plate when on human flesh yielded a value of about 80 ohms.

The advantage of this type of plate is that, when the plate is pulled from the skin, as might accidentally but rarely happen, then the reactive impedance is so sized that as the plate area diminishes, the impedance rises quickly to a value that limits the total current and hence the total power and power density delivered. This effect is shown by the curves in FIGS. 2 and 3 where both the total power and the power density (i.e. power dissipated per unit area of skin) are held to moderate levels in the capacitive type of neutral plate for the maximum power settings on a diathermy machine. Although in this particular case 'safe' limits as shown arbitrarily in these graphs are exceeded, it is evident that the possibility of a severe burn is very much reduced. Indeed a redesign, by for instance thickening the dielectric of the neutral plate, would easily permit 'safe' limits to be held.

Note that a power density of 300 mW/sq cm is about the value at the surface of a 25 cm 60 W incandescent strip light and appears quite bearable to the touch, whereas the power density of 600 mW/sq cm at the surface of a 60 W pearl lamp is distinctly unbearable. Of course there are several complicating factors in the above picture, not least being that the surgeon applies power in an intermittent fashion, which would permit somewhat higher short term power densities. The overall conclusion is, however, that the capacitive type of plate is a fail-safe device in the type of accident where the plate is pulled off.

The other advantage claimed for capacitive type plates is similar to the last-mentioned one, but concerns normal use. In this case it is evident that the plate or adhesive does not actually have to touch the skin to achieve a capacitive value. A much more even distribution of current is therefore likely than from the conductive type of plate, which relies on special preparation to achieve good plate skin contact resistance. Even with the modern self-adhesive conductive types it is possible that current density is higher at the edges than directly under the plate where it might not be so firmly pressed down. In short, hot spots are inherently avoided.

The capacitive type neutral plate has, however, the following disadvantages:

a. Because of the somewhat higher impedance of the capacitive plate as presently manufactured, it does mean that for earth-referenced diathermy machines the patient (FIG. 4) can be at a significant potential, Vf, with reference to earth and any inadvertent contact of the patient to earthed metal could allow current to flow and an RF burn to be sustained (FIG. 4A). Because of the low contact resistance, $Z3$, of the resistive neutral plate, this accident is much less likely to produce a damaging current. For FIG. 4:

$Z5$ represents impedance of alternative internal current path;

$Z6$ represents contact impedance of patient to metal object;

$Z7$ represents impedance to earth of metal object; and $Z8$ represents the overall impedance (mainly capacitive) of the patient to earth.

b. Again because of the high impedance of the capacitive neutral plate any shunt path can carry a current of damaging proportions. Thus if there is a point failure in the insulation, or if an uninsulated tab were to contact the skin then a large proportion of the current could be carried through this failure at very high power density. This path is represented by any impedance in parallel with $Z3$.

The possibility of this type of event occurring has led to this type of neutral plate not being used except for applications below 50 W.

OBJECTS OF THE INVENTION

It is an object of the present invention to provide surgical diathermy apparatus which obviates or mitigates the abovedescribed disadvantages. It is also an object of the invention to provide suitable forms of electrodes and control systems for use with such apparatus.

SUMMARY OF THE INVENTION

According to the present invention there is provided surgical diathermy apparatus comprising a power source, an active electrode for operation on a patient, a capacitive neutral plate for attachment to the patient, and a potential compensator for providing a compensating potential in series opposition to the potential drop across said capacitive neutral plate.

Preferably the apparatus includes a compensation potential level adjuster for adjusting the level of the compensation potential provided by the potential compensator.

Preferably the apparatus also includes an open circuit fault condition detector for detecting open circuit fault conditions of the capacitive neutral plate.

Preferably the apparatus also includes a short circuit fault condition detector for detecting short circuit fault conditions of the capacitive neutral plate.

Most preferably the apparatus includes an alarm system associated with said fault condition detectors and including deactivation means for deactivating the diathermy apparatus. Preferably the apparatus also includes two or more compensated capacitive neutral plates or plate elements which are included in the circuit such as to provide an automatic reduction of current in a faulty plate.

Preferably the apparatus also includes an array of neutral plates or a multi-element capacitive neutral plate such that the statistical probability of a significant fault current occurring is minimised.

Preferably the apparatus also includes an automatic control system for automatic control of the apparatus. The automatic control system is preferably based upon a microprocessor.

BRIEF DESCRIPTION OF THE DRAWINGS

Embodiments of the present invention will now be described, by way of example, with reference to the accompanying drawings, in which:

FIG. 2 is a graph illustraing the power dissipation relative to skin contact area for conventional conductive and capacitive type neutral plates;

FIG. 3 is a graph illustrating the skin power density in relation to skin contact area for conventional conductive and capacitive type neutral plates;

FIG. 19 illustrates the equivalent circuit of a multi-element capacitive neutral plate under fault conditions.

(Note:- FIGS. 1–4 illustrate the background to the invention and have already been described in the "Background of the Invention" section above).

DESCRIPTION OF PREFERRED EMBODIMENTS

Details (Section 1):

IMPROVEMENTS RELATING TO THE CAPACITANCE TYPE INDIFFERENCE PLATE

Figure 5:
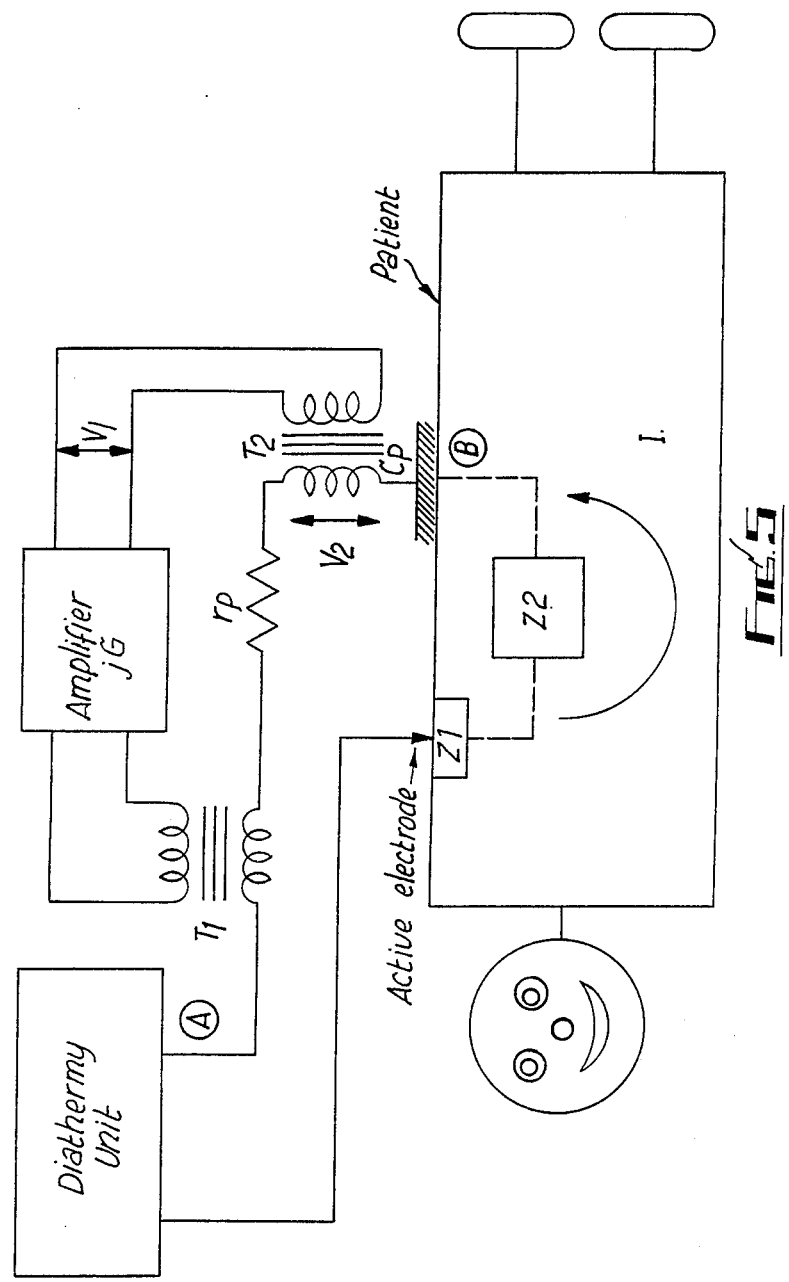
FIG. 5 is a circuit diagram of one embodiment of surgical diathermy apparatus in accordance with the present invention.

This section describes improvements such that the above disadvantages of the capacitive type indifference plate are overcome. The basic improvement is to arrange that voltage is injected in series with the capacitance neutral plate of such a value that it equals or nearly equals the potential drop across the capacitive reactance. FIG. 5 shows the basic arrangement and the following equations describe the effect:

$$V_{AB} = Ir_p + V_2 + I/jwC_p \quad (3.1)$$

$$= Ir_p + \frac{jGI}{q_1 q_2} + I/jwC_p \quad (3.2)$$

$$= I[r_p + j(G/q_1 q_2 - 1/wC_p)] \quad (3.3)$$

where w is the angular (radian) frequency of the diathermy set, $V_{AB}$ is the potential drop between points A and B, r residual resistance, C capacitance and p the subscript denoting that these quantities refer to the plate circuit. Also $V_2$ is the injected voltage which is derived from the amplifier (or other electronic power source slaved to the generator) which device not only provides gain G but also provides 90° phase shift with respect to the current, I, and current to voltage conversion. $T_1$ is a current sensing transformer with a step down turns ratio of $q_1$ so that the amplifier delivers a signal $V_1$ as follows:

$$V_1 = \frac{jGI}{q_1} \quad (3.4)$$

The current in the secondary of the transformer $T_1$, namely $I/q_1$ is set by $q_1$ so that any reference resistor in the amplifier need only be a low wattage type, but at the same time high enough to give a sufficient signal at all times. Similarly transformer $T_2$, a voltage step down type of ratio $q_2$ in relation to the amplifier output signal, $V_1$, affords protection to the amplified output by reducing backward current injection from the main circuit into the output of the amplifier. The injected voltage $V_2$ is given by:

$$V_2 = V_1/q_2 = \frac{jGI}{q_1 q_2} \quad (3.5)$$

Since $V_2$ is arranged to be equal or nearly equal in magnitude to $I/jwC_p$, compensation of the neutral plate capacitance, $C_p$, takes place such that for a given value of I, $V_{AB}$ is minimised.

Disadvantage b. (background section above) is now removed or nearly so since according to equation (3.3) the worst case potential of the patient with respect to earth is $I_{max}.r_p$ where $I_{max}$ is the maximum diathermy current and since this is usually around 1 Ampere, the worst case potential will be quite small.

If we assume that in practice the injected voltage $V_2$ has a 10% mismatch with a capacitive plate potential drop of 80 volts, then the value of $V_{AB}$ is about 8 volts. If the patient makes contact with an earth path with a contact area of 10% of that of the neutral plate, i.e. 20 sq cm and ten times the postulated contact resistance, or 20 ohm, then the current through the patient due to the earth path would be 0.4A and the power density would be about 160 mW/sq cm which appears to be very safe according to the previously adopted limit of 300 mW/sq cm. So, on a conservative estimate the improved circuit renders the earth-referred diathermy safe. A more thorough analysis is presented in the Appendix below.

However there is also concern with the case where the plate incurs either a failure in use or a failure in manufacture such that the insulating material breaks down at a point such as to have a low value resistive path. In effect the capacitance of the neutral plate is shorted out. In the conductive type plate this would mean high current and power densities at the point failure with a high chance of a burn to the patient. With the invented circuit however, it can be arranged so that this does not happen. For if the capacitance is shorted out the cancelling effect is removed and the injected potential, $V_2$, becomes $V_{AB}$, the potential developed across points A and B as shown in FIG. 5. This effect can be used in different ways as described below.

This arrangement is more elaborate than the inductive compensation circuit (FIG. 6) but it affords easier and more reliable means of automatic control as described below.

The required injection voltage could be derived by different means—e.g. from the output voltage of the diathermy unit—and via different coupling methods—e.g. optical or capacitance—but the general principle of achieving an injection voltage proportional to the current, is the substance of the idea here presented.

Figure 6:
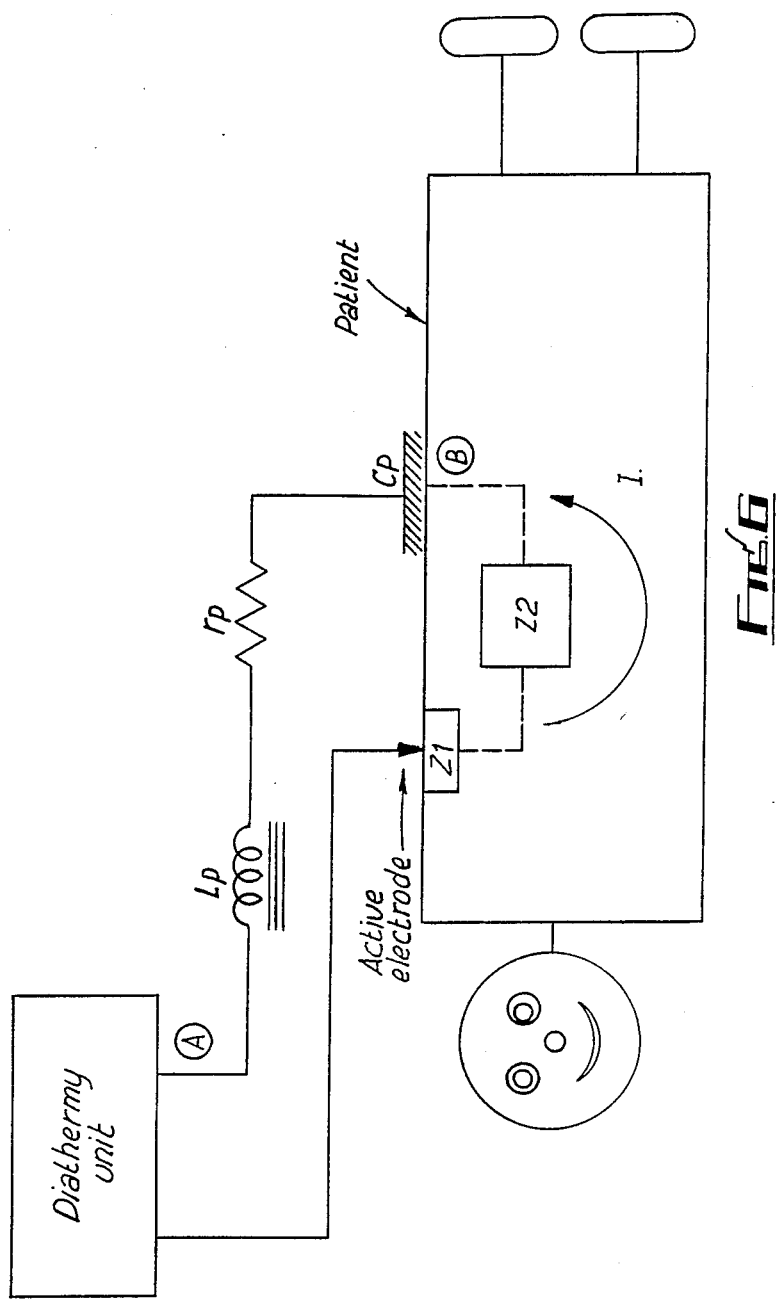
FIG. 6 is a circuit diagram of a further embodiment of surgical diathermy apparatus.

Also, a mixture of the two techniques, i.e. the voltage injection method of compensation as described herein, and the inductive compensation method (as shown in FIG. 6) can be employed. By this method the bulk of the neutral plate capacitance can be compensated for by a series inductance and the remainder by voltage injection also in series. Although this method would permit relaxation of the design of the amplifier since the power handling would be reduced, it is not discussed further for simplicity of presentation. The general principles discussed herein would be equally applicable.

The more severe restraint where we have only a partial short is described in the Appendix. Here it is useful to note that the form of equation (3.3) above and the impedance terms therein are similar in form. In particular an equivalent inductance can be defined:

$$wL_p = \frac{G}{q_1 q_2} \quad (3.6)$$

This allows the earlier equations to apply with equal validity in this case. The proviso is made that since, although gain G may be made frequency dependent, it does not in this application need to be made so, since operation is almost invariably at a fixed value of w, say $w_o$. Particular reference is made to the equations in the Appendix below, because it may be taken that all the inductances therein represent compensating injection voltages.

Details (Section 1.1):

THE SINGLE CAPACITANCE NEUTRAL PLATE

Figure 7:
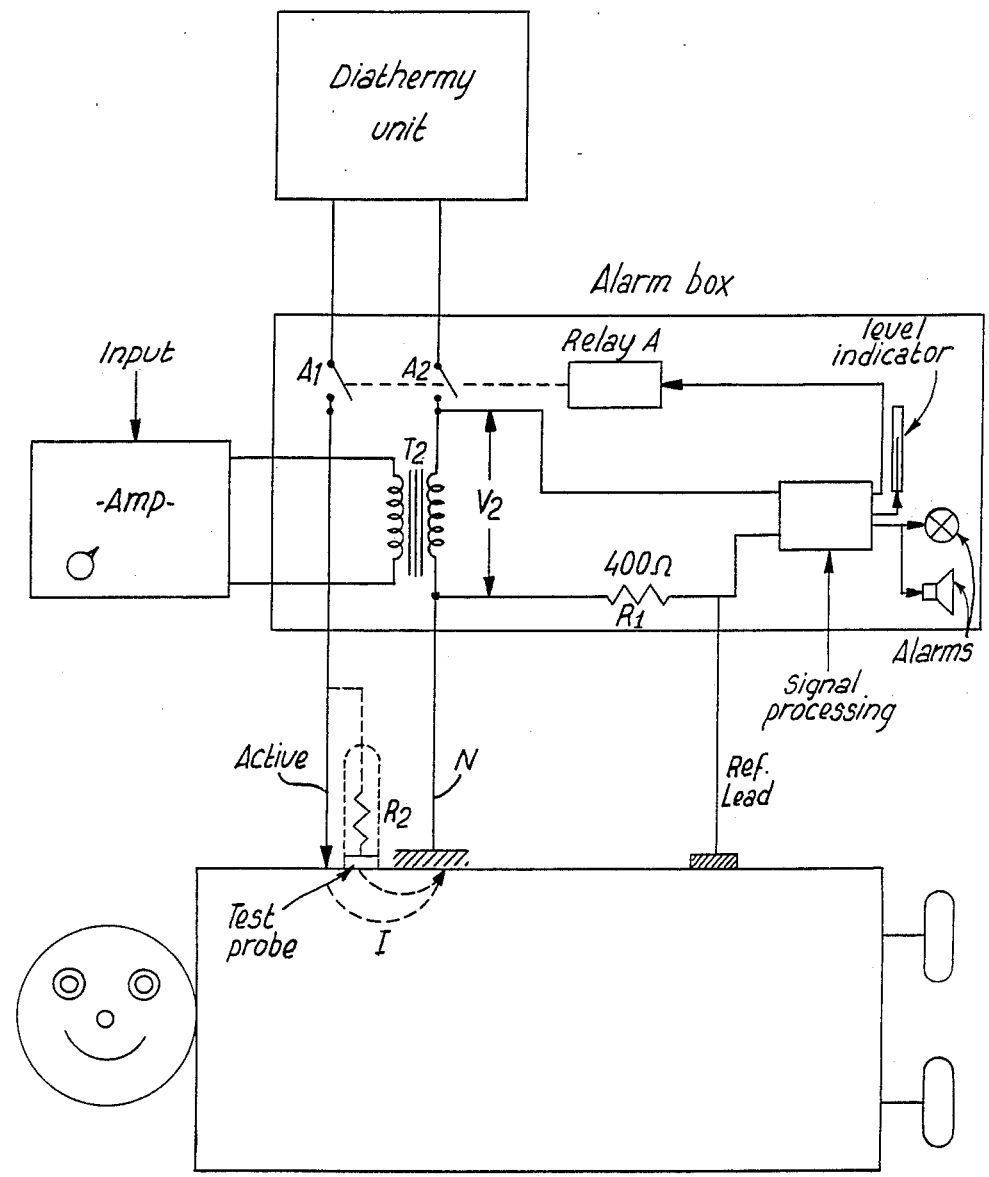
FIG. 7 is a circuit diagram of surgical diathermy apparatus of the present invention incorporating an alarm circuit.

The arrangement for this version is shown in FIG. 7. This shows a suggested arrangement of a diathermy unit connected through a patient via an alarm box which is specifically designed to detect a fault in the capacitance plate and disconnect the diathermy from the patient. It is here assumed that the diathermy is of a type which has no arrangement for detecting plate continuity—i.e. for detecting whether the conventional type neutral plate is not sufficiently adhering. In addition to the usual active and neutral leads a reference lead is required in order to establish the reference potential of the alarm box detection circuits at a value near to that of the patient's body. Thus the potential presented to the signal processing section of the alarm box is that of the injected potential in series with the potential drop across $C_p$.

The reference lead thus has to be attached to the patient by means of a small adhesive and electrically conductive pad. This could be either integral with the neutral plate or be a separate pad similar in type to those used in e.c.g. measurements, but placed close so that it takes up a correct potential.

To operate this diathermy system the surgeon or assistant would first of all take the active lead fitted with a dummy probe and touch it on a test pad. He would operate his foot switch and set the diathermy control to obtain a suitable power level. By operation of push buttos or continuous adjustment the amplifier gain is varied so that the level indicator now shows a maximum. In this way the capacitive reactance, Cp, of the neutral plate is matched. Note that the current path is:- R2, patient, Cp, neutral lead, the secondary of $T_2$—and is limited to a safe value by R2. Contacts A1 and A2 are normally closed.

The surgeon now proceeds in his usual way. The current then flows—active lead, patient, Cp, neutral lead, secondary of $T_2$. As already described, if Cp experiences a fault and the current is above 0.3A, then a threshold potential of $V_2$ of say 24 v, would be exceeded. The signal processing electronics would detect this event, alarm lights or sounders would be activated, the level indicator would indicate high or danger and the relay would be activated to open contacts A1, A2 and disconnect the supply to the diathermy unit.

To guard against the event of the reference lead being pulled off its conductive pad, a resistor R1, at a value sufficiently higher than the reactance of Cp (say 400 ohm) not to draw significant current in normal operation, but low in relation to the input of the signal processing electronics, is placed across the neutral and reference leads as shown in FIG. 7. If the reference lead or pad becomes disconnected, only the potential $V_2$ would be detected and the alarms and relay would be operated as above. Alarm circuits would latch on and have to be reset after appropriate corrective action.

Neither details of the signal processing nor power supply are shown as these could be conventional. Suffice it that a high level of isolation from mains power is required. The box could be a separate unit or a retrofit to an existing diathermy unit. British Standard BS5724 has to be observed. Values shown are indicative and would be subject to alteration as circumstances require.

Figure 8:
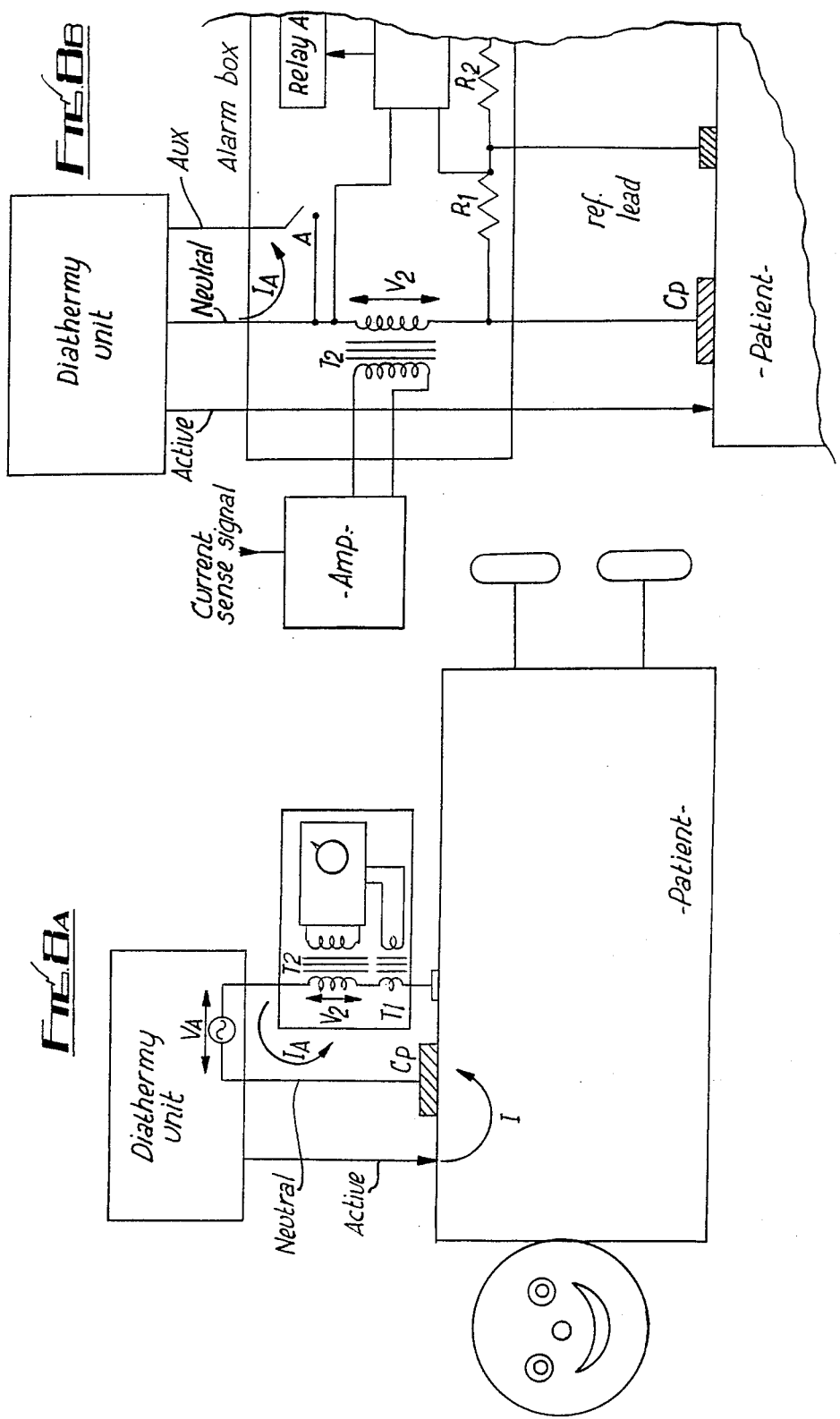
FIGS. 8A and 8B illustrate surgical diathermy apparatus of the present invention incorporating a plate continuity alarm.

Suggested variations of the single neutral plate system are shown in FIG. 8, which shows arrangements suitable for diathermies which have an intrinsic alarm for plate continuity. This type of alarm uses a two element neutral plate and operates when the resistance between the two elements and through the patient rises above a predetermined value. In Eschmann machines this is detected when the current, from an auxiliary oscillator operating at 30 kHz and in a separate neutral plate loop, falls below a preset threshold.

This type of alarm may be adapted as in FIG. 8 to detect an increase in the impedance of the loop. In FIG. 8A the current $I_A$ is injected into the above mentioned loop operating at a radian frequency of $w_o$. The compensating amplifier, compensating transformer $T_2$ and sensing transformer $T_1$ are contained in an auxiliary box with its own set of leads. The auxiliary current is given, by analogy with equation (3.3), by:

$$I_A = V_A/[r_p + j(G/q_1q_2 - 1/W_oC_p)] \quad (3.7)$$

The amplifier gain could be set by similar means to those described above and in FIG. 7. If perfect balance were to be achieved equation (3.7) would become:

$$I_A = V_A/r_p \quad (3.8)$$

This would be a rather large current and would simulate the low resistance condition of the diathermy set's loop integrity circuit. However if the neutral plate were to be flawed—in the extreme shorted—then equation (3.7) would approach:

$$I_A = V_A/(jG/q_1q_2) \quad (3.9)$$

Since $w_o$ now relates to a frequency of 30 kHz, the neutral plate reactance would now be between 600 and 2000 ohms and therefore so also would be the synthetic reactance in the denominator of equation (3.9). $I_A$ would drop to a low value, thus simulating the open plate condition of the diathermy and so the diathermy current I would be shut off. FIG. 8B shows the arrangement of FIG. 7 again, with the exception that the relay acts on the contact A which is in the plate continuity detection circuitry.

These more elaborate circuits could become most attactive for fixed installations which already lack an alarm feature i.e. the plate potential alarm. Retrofitting of one of the above mentioned circuits could be most economically carried out if this alarm feature was also installed at the same time.

Another advantage of the capacitance plate already mentioned is that it can also be designed such that if it is peeled off by some error, then the impedance (capacitive reactance) of the plate rises to limit the current to a safe value. This value probably depends on a threshold of power (from a near-point scource) which can be dissipated harmlessly into the mass of surrounding flesh. Considerations of available point sources such as cautery burners and small lamps seem to suggest a threshold of about 1 Watt before pain ensues, although one make of diathermy specifies a tolerance of 7 W presumably inclusive of zero setting. It is also hard to envisage that the capacitive plate would form a point source. Rather there would be small area (of about say a quarter of a sq cm) below which the plate would fall off completely.

Figure 1:
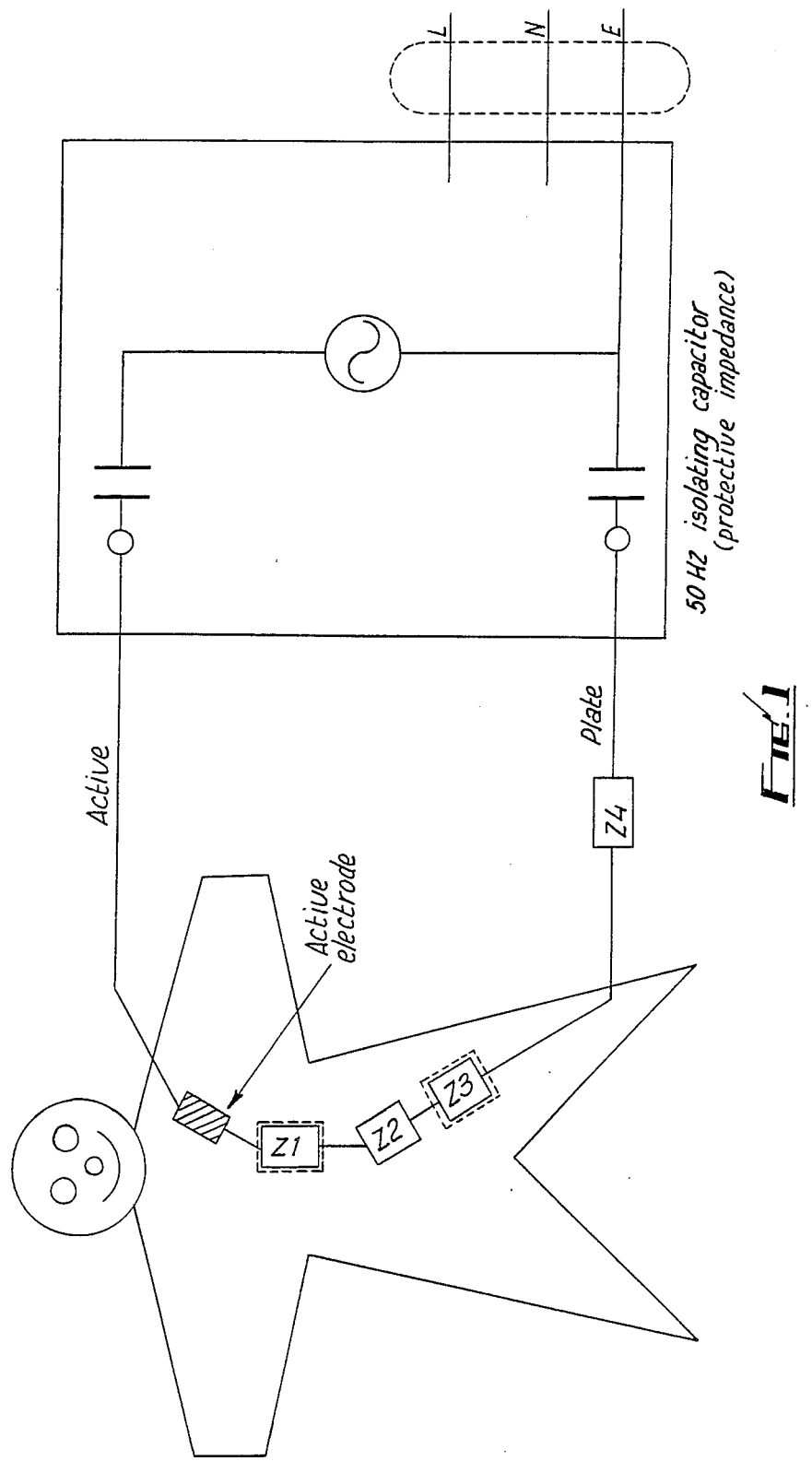
FIG. 1 is a schematic diagram illustrating a typical layout of conventional diathermy apparatus.
Figure 4A:
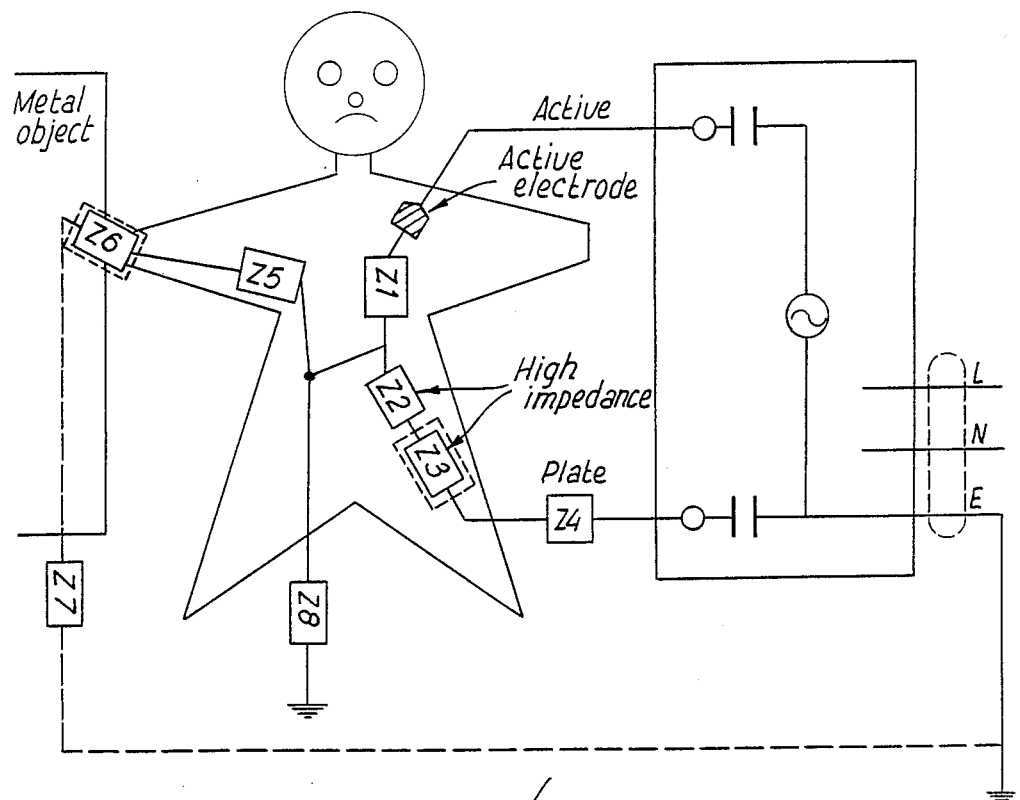
FIG. 4A is a schematic diagram illustrating a potential fault condition of a capacitive neutral plate circuit.
Figure 4B:
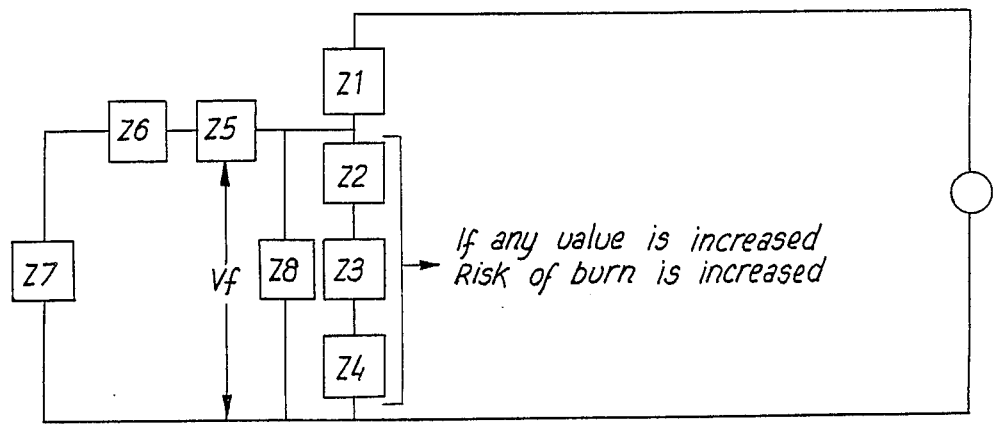
FIG. 4B is an equivalent circuit diagram of the schematic of FIG. 4A.

The design of the plate would accord with the following considerations. Assume Z3 in FIG. 4 is made up of a 'contact' resistance, $r_c$, and the capacitive reactance $X_c$. Assume $r_c$ is 2 ohm as in FIG. 4, then for a fault condition where only 0.25 sq cm of the plate is adhering and the whole plate has an area of 180 sq cm. Then $r_{fc}$, the fault contact resistance would be:

$$(180/0.25) \times 2 = 1440 \text{ ohm}$$

For a fault current, $i_f$ we wish:

$$i_f^2 \, r_{fc} < 1 \text{ Watt} \quad (3.10)$$

i.e.

$$i_f < 26.4 \text{ mA}$$

If $X_{cf}$, the fault capacitive reactance, is designed to be the current limiting impedance from a generator e.m.f. of 800 v, then we obtain:

$$X_{cf} = 800/i_f = (800/0.0264) = 30,000 \text{ ohm} \quad (3.11)$$

The design reactance is given by the ratio of the areas already assumed, fringing effects being as elsewhere in this specification ignored:

$$X_c = X_{cf} \times (0.25/180) = 42.2 \text{ ohm} \quad (3.12)$$

On this reasoning, the measured reactance of about 80 ohm is more than adequate to limit current to a safe value in the "tear off" situation. If other starting values are shown to be more valid, these can be substituted in the above equations to obtain other design values. Confirmation of these assumptions could be obtained by experimental work.

The current could also be limited for the second type of fault—i.e. a capacitive neutral plate short, since the compensation injection voltage (or inductance) would also have to be high. So, if we were to abandon the present commercial design and were to accept an alteration in the plate physical design then the simple circuits of FIGS. 5 and 6 could form the basis of an intrinsically safe circuit against the two faults discussed. The condition that requires to be satisfied is that, if the plate is shorted out, the current is limited by the compensating voltage $V_2$, which by equation (3.6) is equivalent to $IwL_p$, where $L_p$ is an equivalent inductance.

If we assume that the diathermy excitation voltage is 800 v, that a safe maximum current is 0.25A and that both diathermy source impedance and Z2 are 400 ohm resistive, then the maximum equivalent inductive reactance is given by:

$$(2 \times 400)^2 + (wL)^2 = (800/0.25)^2 = 3200^2$$

i.e. $wL = [3200^2 - 800^2]^{\frac{1}{2}}$
$= 3100$ ohm = the value of the capacitive plate reactance i.e. $V_2 = 3100 \times 0.25 = 775$ v The patient is now exposed to a third hazard, since he would now be at a high potential and in danger of drawing curent through the sneak path (see FIG. 4) by chance contact through an earthed metal object while also being attached to an earth referred diathermy. Utilisation of disconnect/alarm circuits such as those of FIGS. 7 and 8 would solve this problem for single plate sets. For the multi-element or multi-plate circuits described below, intrinsic safety is approached for this hazard since the good compensated branches strap the patient to a small potential with respect to the low voltage side of the machine. Nevertheless the high potentials indicated would impose high demands on the specification of equipment and compromises might have to be made.

To resume the design of the plate, if we take 80 ohm as the reactance of the present plate, which has an adhesive film of 0.004 inch (or 0.1 mm) then the design thickness of the new plate would be approximately:

$0.1 \times (3200/80) = 4$mm or about 0.16 inch

Figure 12:
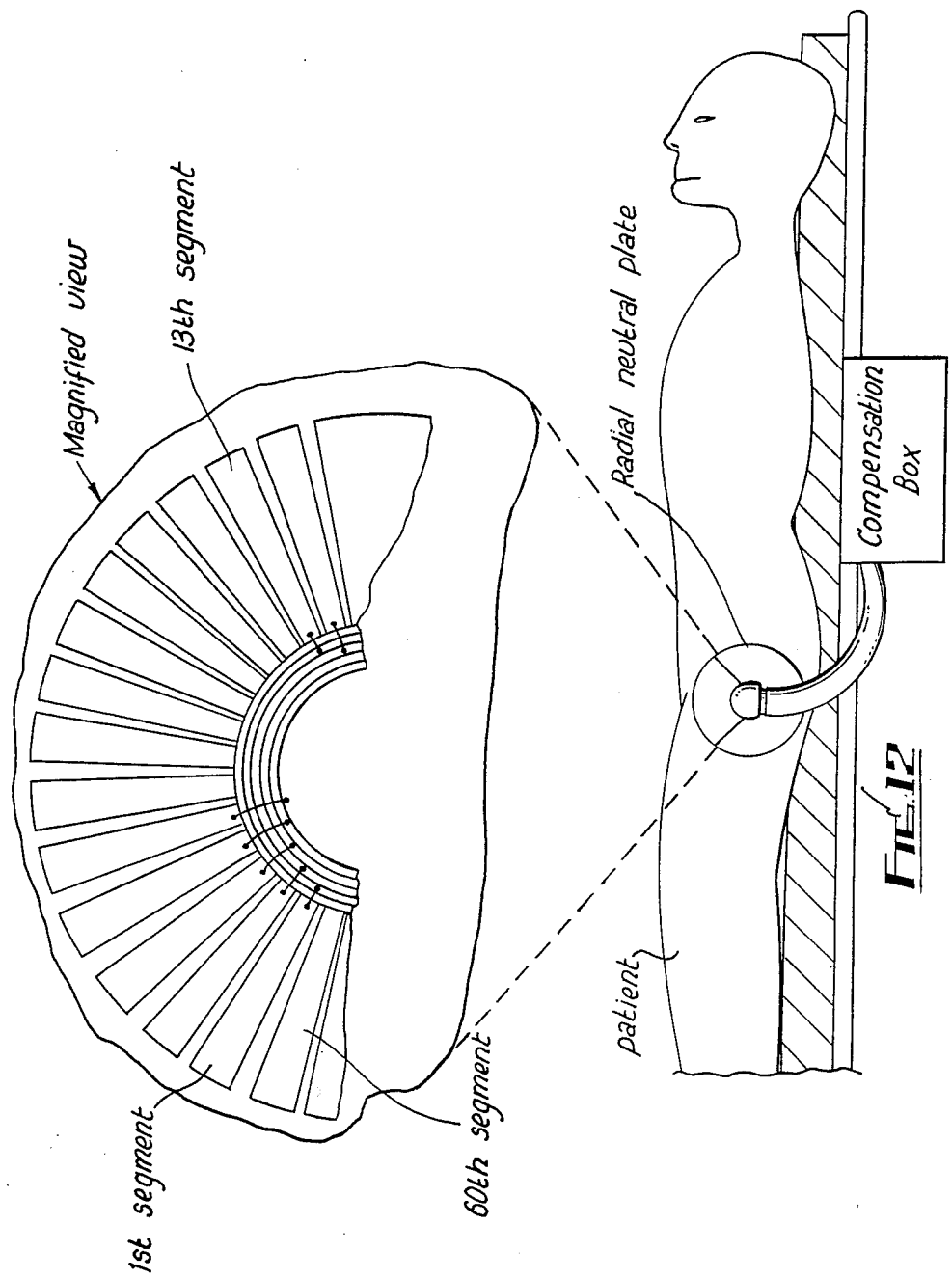
FIG. 12 illustrates one embodiment of a multiple element capacitance neutral plate.
Figure 13:
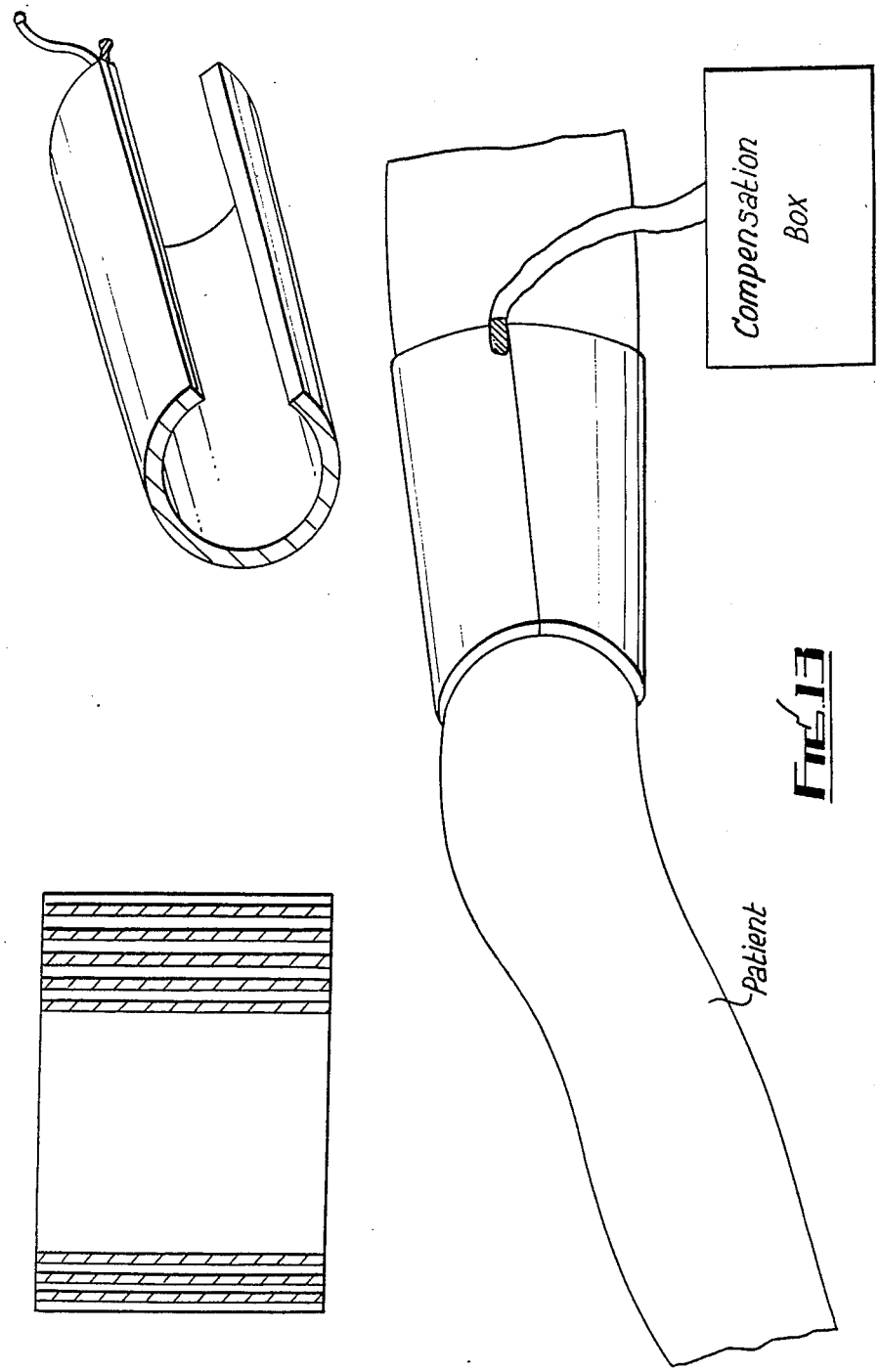
FIG. 13 illustrates a second embodiment of a multiple element capacitance neutral plate.
Figure 14:
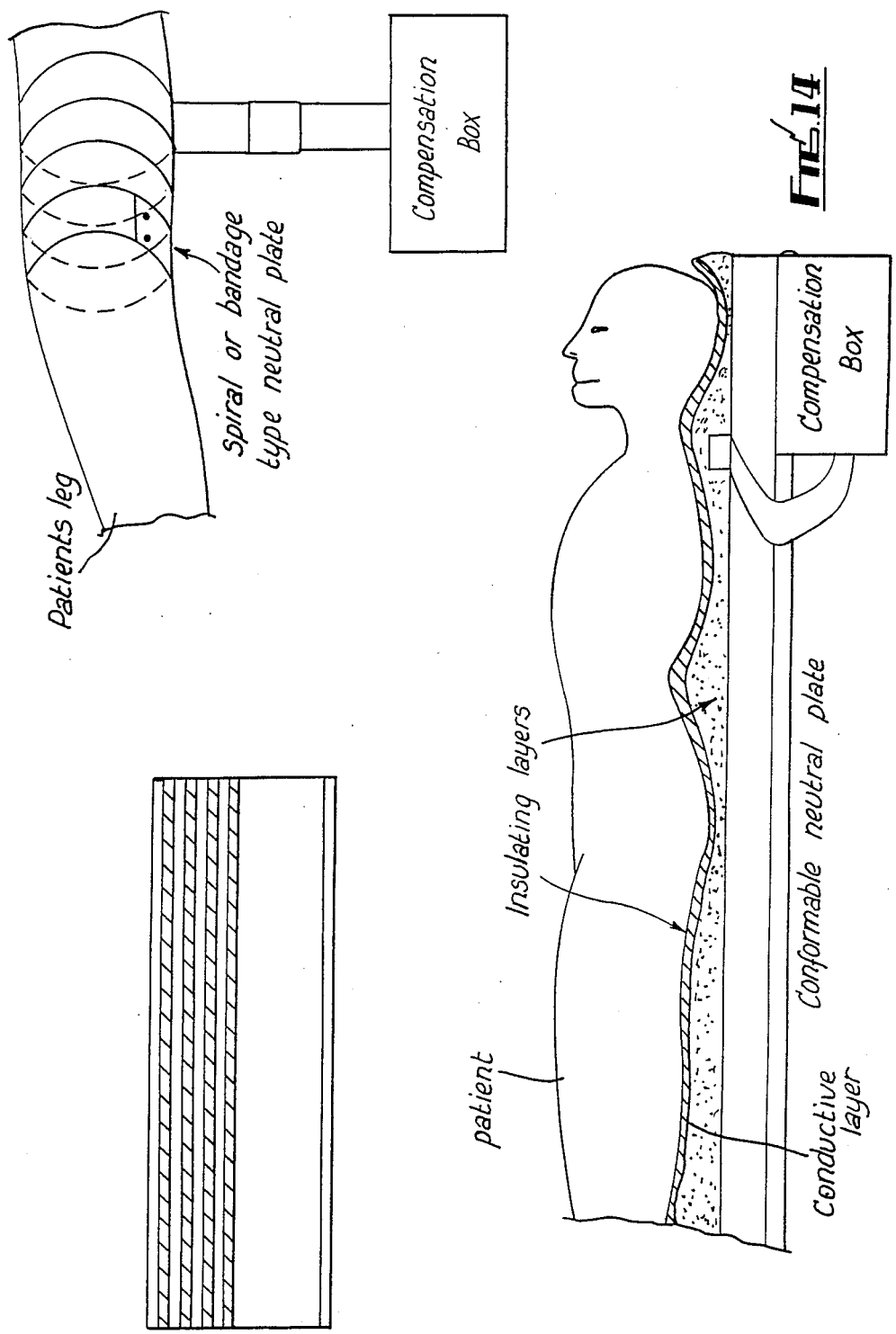
FIG. 14 illustrates a third embodiment of a multiple element capacitance neutral plate.
Figure 15:
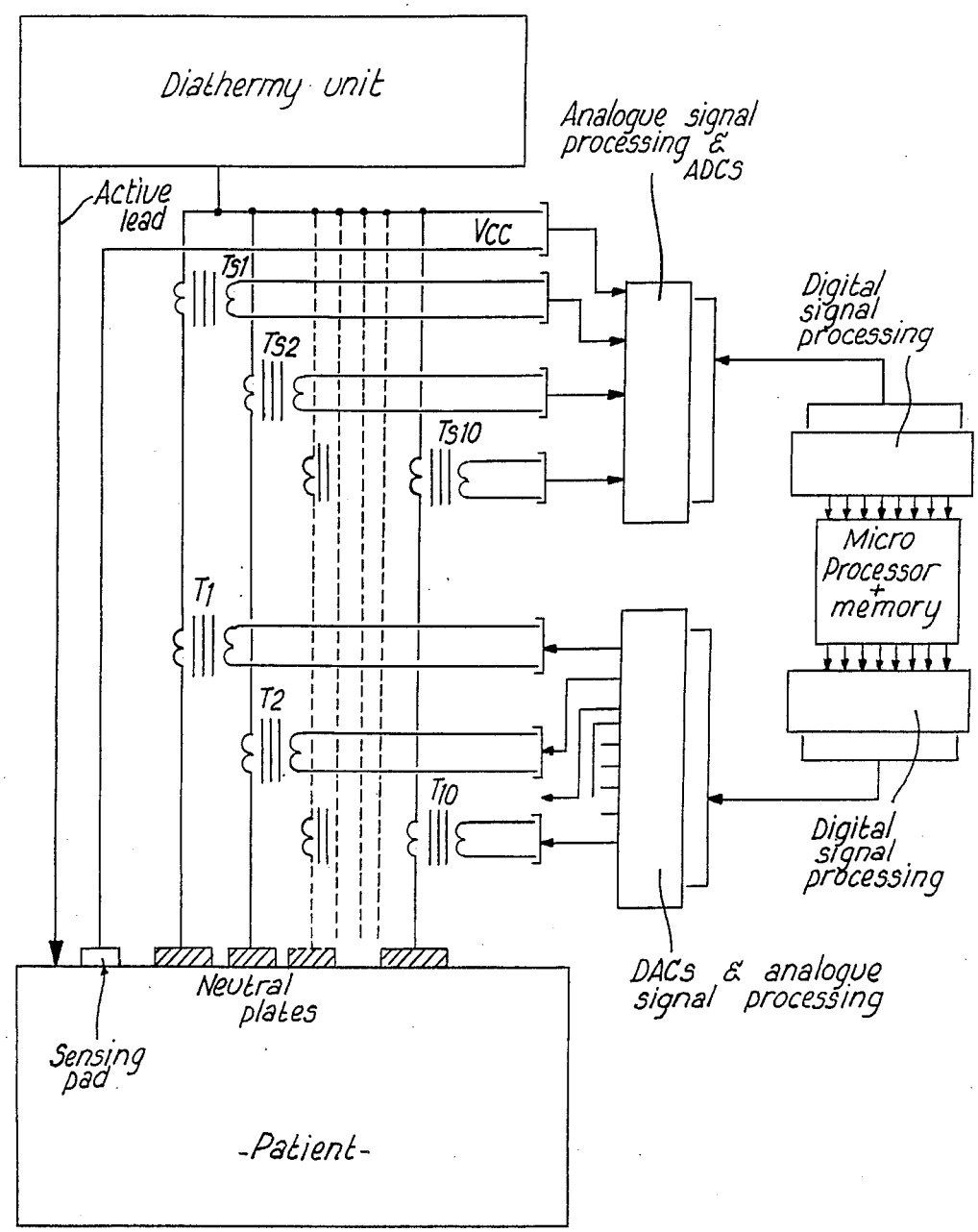
FIG. 15 is a schematic diagram of microprocessor controlled surgical diathermy apparatus in accordance with the present invention.

This is a considerably different type of plate since it would be thicker yet still be flexible to fit different body shapes. However possibilities are opened up for different types of plate of strip or spiral type. Not only thickness but area and shape could be altered. FIGS. 12, 13 and 14 show some general concepts for these designs.

An advantage of the capacitive type of plate is that, since good electrical conductivity is not required no shaving or scrubbing of the skin need be required. A good reactive value is obtained so long as good proximity with the skin is obtained.

The main disadvantage of these plate systems is the requirement for the setting up procedure already mentioned above. The surgeon or assistant would adjust this while using a flat probe and at a low setting (see FIG. 7) so that a peak in current was obtained. A faulty plate would show up as a low curent unable to be peaked. It could then be changed. During surgery any fault current across the neutral plate would be limited as mentioned by $V_2$. However as discussed later control techniques could eliminate this disadvantage.

Details (Section 1.2):

THE DUAL CAPACITANCE NEUTRAL PLATE

The disadvantages of the conventional type neutral plates as described in the last section are:
 (a) they require an additional reference lead; and
 (b) special circuitry is required to disconnect power in the event of a fault.

Figure 9:
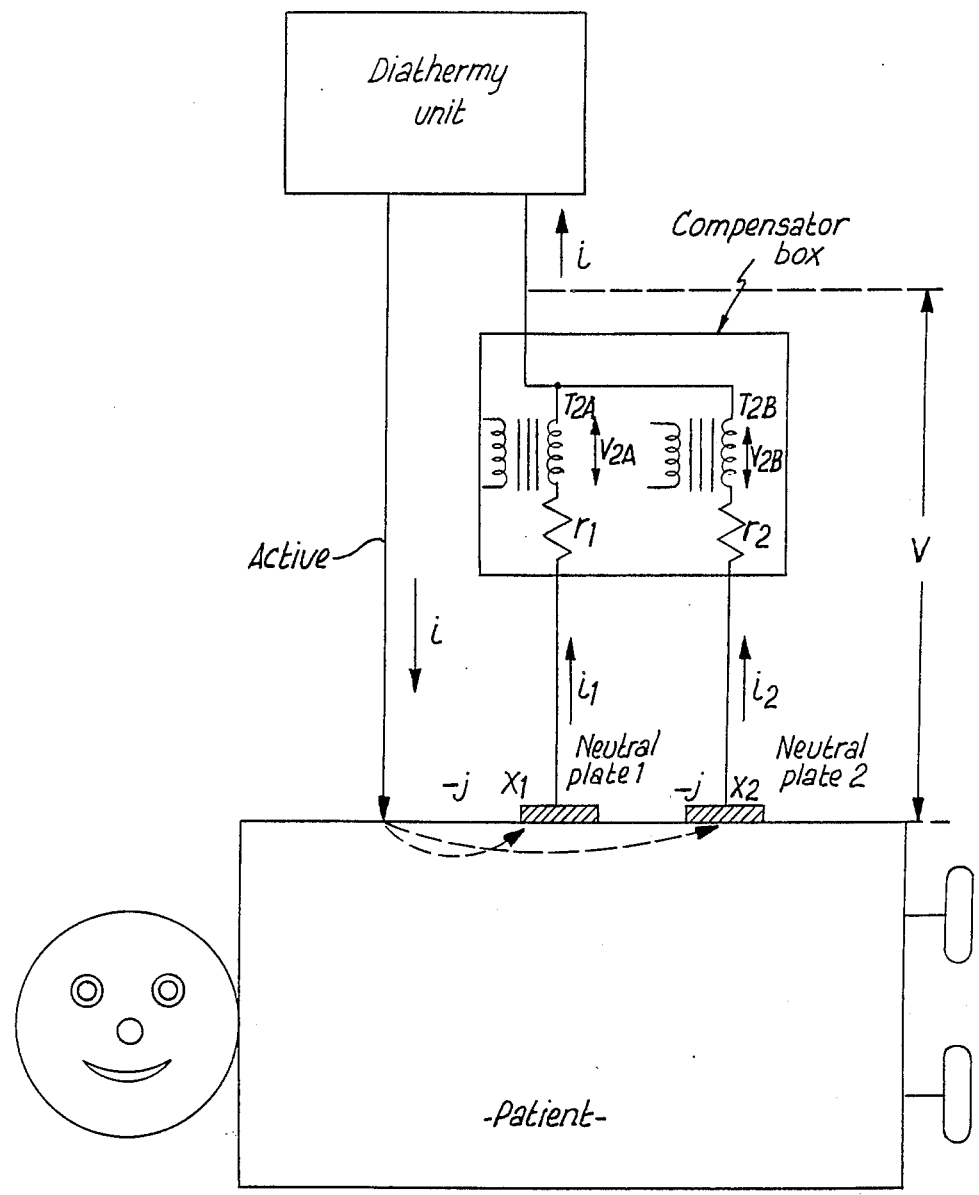
FIG. 9 is a circuit diagram of dual capacitive neutral plate diathermy apparatus of the present invention.

A development of the basic circuit, which could permit the utilisation of present commercial plates and also in some measure be intrinsically safe, is shown in FIG. 9. Here a box containing two amplifier/transformers is placed in the neutral plate circuit. The main current is split into two parallel paths ($i_1$ and $i_2$) which flow through the transformer secondaries and neutral plates. In each path the current is sensed as already described above so that the equivalent inductances representing the injected voltages, $V_{2A}$, $V_{2B}$ (see equations 3.5, 3.6 earlier) balance the negative reactance of the neutral plate.

This condition is described by the following equations:

$$V = jwL_1i_1 + i_1r_1 - jX_1i_1 = V_{2A} + i_1r_1 - jX_1i_1 \quad (3.13)$$
$$= jwL_2i_2 + i_2r_2 - jX_2i_2 = V_{2B} + i_2r_2 - jX_2i_2$$
$$= i_1r_1 = i_2r_2$$

where $r_1$ and $r_2$ are the values of the winding resistances of each inductor. At maximum diathermy current, if $r_1$ and $r_2$ are about equal, then:

$i_1 = i_2 = 0.5A$

However a wide tolerance on resistance and thus current is acceptable.

Under the condition, say, that neutral plate 2 shorts out, then $jX_2$ becomes zero and the equation now becomes:

$$V = ir_1 = i_2(jwL_2 + r_2) \quad (3.14)$$
$$= i_2jwL_2 = i_2jG_B/q_{1b}q_{2b} = V_{2b}$$

i.e.

$$i_2 = i_1r_1/jwL_2 \quad (3.15)$$

If we suppose $r_1$ is about 4 ohm and $jwL_2$ about 80 ohm, then $i_2$ is about a twentieth of $i_1$, or less then 50 mA for full power where i is 1 Amp. Note that V would be $1 \times 4 = 4$ v and $V_{2B}$ would be $80 \times 0.05$ also 4 v and the patient thus be at a very low potential with respect to the generator low terminal. Similar results would be obtained with the high reactance plate of the last section and so the patient would be safe from this hazard. A similar result is found if the other neutral plate shorts. That is, the bulk of the current is forced down the good neutral plate, while the current of the damaged plate is held at a safe level.

This is an important feature of this and the other compensated multi-plate circuits and is the basis of their inherent safety.

Since the expected average incidence of flawed plates is not known a method is suggested to take care of the simultaneous appearance of two flawed neutral plates. The circuitry of FIG. 9 would not now be sufficient since at least one of the fault plates could now be carrying 0.5A or more at full power.

Figure 10:
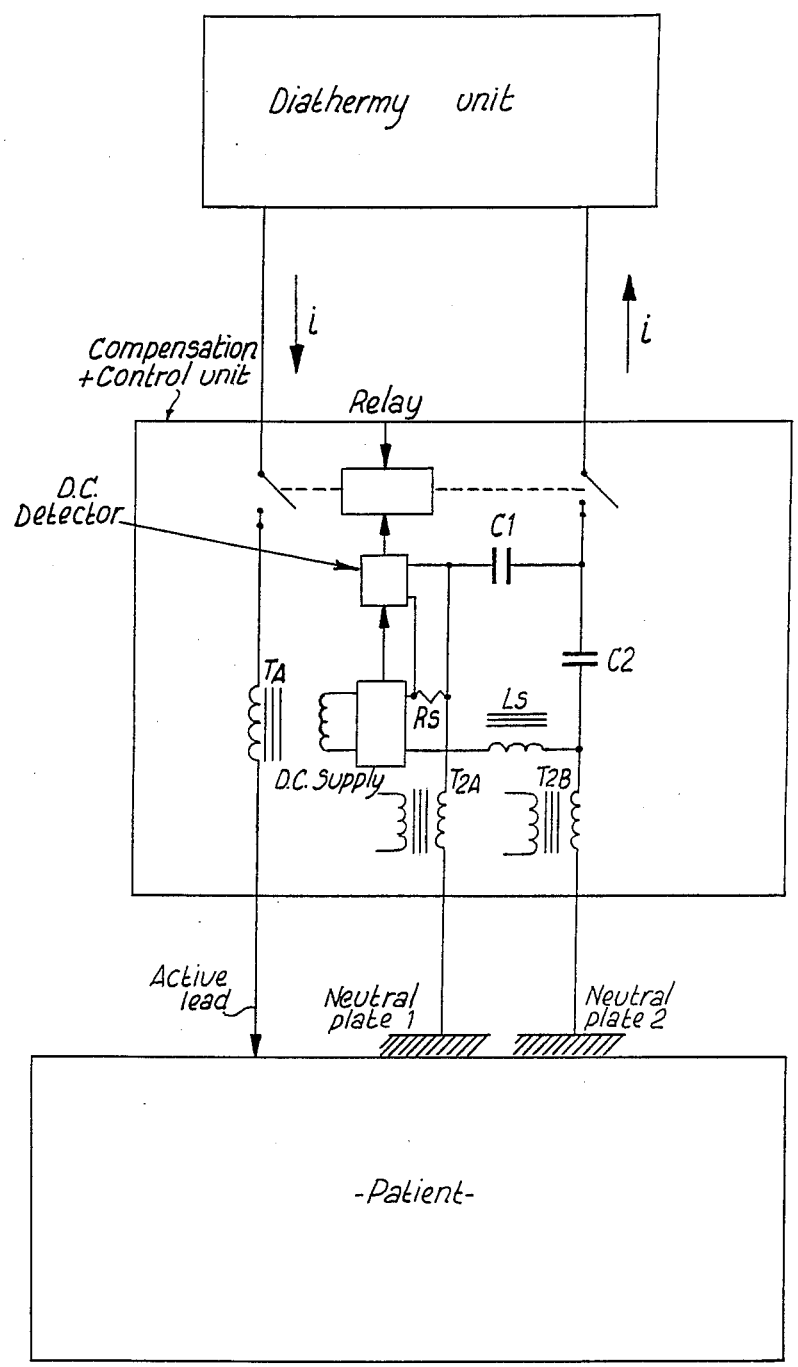
FIG. 10 is a circuit diagram of dual capacitive neutral plate diathermy apparatus incorporating a fault detecting circuit.

A method of solving this problem is suggested in FIG. 10. A d.c. supply is derived from a transformer $T_A$. $L_S$ is of sufficient value that R.F. current does not feed back into the d.c. supply. As the current in the primary of $T_A$, i.e. also in the neutral plate line, is increased, so also is the level of the d.c. supply. In normal operation litle or no current is drawn from this supply, because $C_1$ and $C_2$ block d.c. current in the upper loop of the double plate circuit, while so long as the plates are intact no current is drawn in the lower loop. Even if one of the plates shorts, the other will still block d.c. current.

However, in the rare event that both plates short, a current is drawn, a p.d. is developed across $R_s$ and the disconnect and alarm circuits are triggered. Much detail is omitted for clarity.

Of course to take care of the double fault eventuality it is again necessary to sacrifice simplicity.

Details (Section 1.3):

THE MULTI-ELEMENT NEUTRAL PLATE

Figure 11:
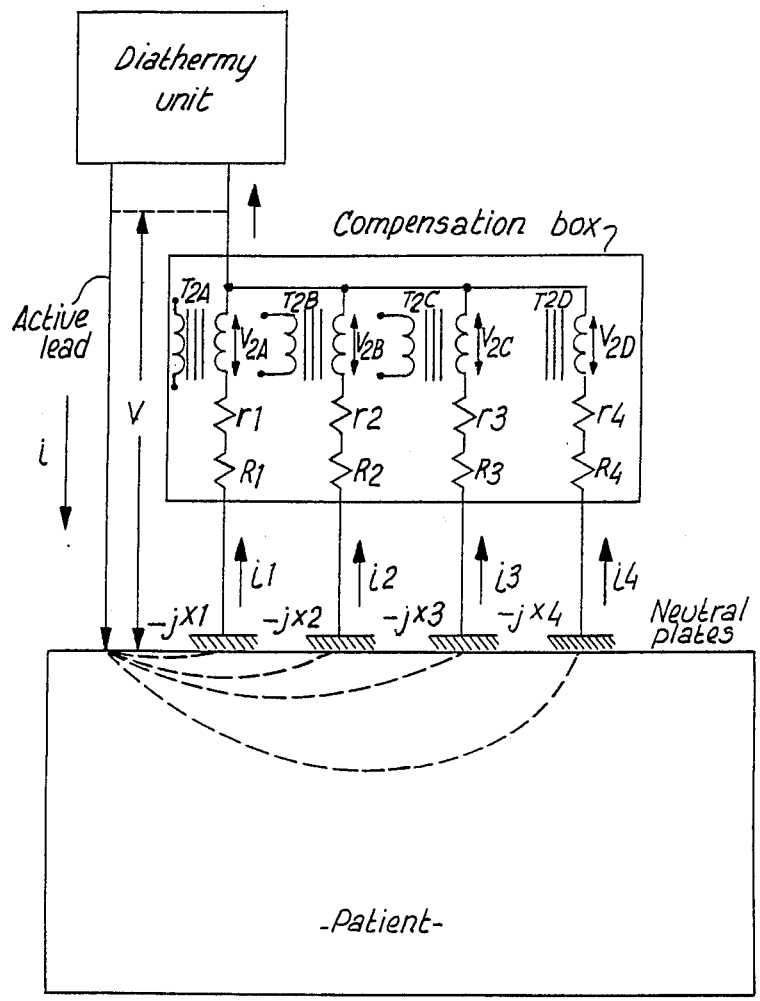
FIG. 11 is a circuit diagram of multiple element capacitance neutral plate surgical diathermy apparatus.

Another approach to the handling of simultaneous faults is the now introduced concept of a multi-element neutral plate. It is an extension of the dual neutral plate and could consist of many small plates similar to e.c.g. plates. Alternatively it could be a single device built up as a sandwich of insulating layers enclosing a conductive layer, which would be divided into small metal or other conductive plates. FIGS. 12, 13 and 14 show some notional designs while FIG. 11 shows a 4 element circuit.

The advantages of the capacitive neutral plates as seen so far might be listed as follows:

(a) can be designed to be intrinsically safe from the peel-off fault condition;

(b) can be designed to be intrinsically safe against the punch through or short circuit condition;

(c) simpler preparation of the patient's skin, since adhesion not required for good electrical conductance; and (d) the promise of economies since it may be possible to design a re-usable capacitance neutral plate.

However advantage (b) is conditional on either the feasibility of close tolerance matching of the p d. across the neutral plates and their compensating voltages or the possibility of precise adjustment of that compensating voltage through say the setting of amplifier gain. It has also been assumed that any plate fault is a dead short. In addition there is no data on the incidence of faults in capacitive neutral plates. Where the elaboration of additional circuitry described in the previous sections for either the single or the dual capacitance neutral plate is unnacceptable, the multi-plate capacitance neutral plate promises a simpler approach.

The following calculation illustrates how a multi-element plate reduces the statistical incidence of a fault to negligible proportions. Repeating the format of equation (3.10) in section 3.1, but using a contact resistance $r_c$ of say 20 ohm, we might wish to limit the power dissipation to 1 Watt. This gives, where $i_{mmax}$ is the maximum current in a branch, m:

$$(i_{mmax})^2 r_c = 1 \text{ Watt or} \quad (3.16)$$

$$i_{mmax} = 0.224 \text{ A say } 0.2 \text{ A}$$

Since the total delivered maximum current is typically 1 Ampere from a diathermy machine, this implies a minimum of (m=5) good branches to share current; m could be made equal to 1, but this assumes a large area element to achieve a low value of $r_c$, and would leave little safety margin. So, if a failure rate is now postulated at 1 in 20 for the neutral plates (i.e. probability=0.05) then we can stipulate an extra number of sacrificial elements, n, such that the probability of all of them failing at once is extremely low. If n is 5 then this probability is 3 in 10 million. If this were an acceptable risk, then the design number of elements would be 10.

A four-element plate is assumed in the following simple analysis (See FIG. 11), while in the Appendix the case of partial shorts is analysed. This more complex analysis allows for tolerance variation and illustrates the design criteria to be considered.

In the following analysis, a set of power resistors, $R_1 R_2 R_3$ and $R_4$, all of value 5 ohm, ensure aproximately equal current division. The equations describing normal working are:

$$(3.17)$$

$$\begin{aligned} V &= i_1(R_1 + r_1 + jwL_1 - jX_1) = i_1(R_1 + r_1) \\ &= i_2(R_2 + r_2 + jwL_2 - jX_2) = i_2(R_2 + r_2) \\ &= i_3(R_3 + r_3 + jwL_3 - jX_3) = i_3(R_3 + r_3) \\ &= i_4(R_4 + r_4 + jwL_4 - jX_4) = i_4(R_4 + r_4) \end{aligned}$$

where the equivalent inductive reactances therein are equal in turn to $V_{2A}/i_1$, $V_{2B}/i_2$, $V_{2C}/i_3$, $V_{2D}/i_4$, and $i_1 = i_2 = i_3 = i_4 = 0.25$ A.

Suppose now one plate shorts, say plate 1, then equations (3.17) become:

$$\begin{aligned} V &= i_1(R_1 + r_1 + jwL_1) \\ &= i_2(R_2 + r_2) \\ &= i_3(R_3 + r_3) \\ &= i_4(R_4 + r_4) \text{ and} \end{aligned} \quad (3.18)$$

$$i = i_1 + 3 i_2$$

or to a first approximation, i.e. if $jwL_1 >> R_1 + r_1$:

$$i_1 jwL_1 = i_2(R_2 + r_2) = [(i - i_1)(R_2 + r_2)]/3 \quad (3.19)$$

i.e. $i_1 = i(R_2 + r_2)/3jwL_1$

If $$jwL_1 = 120 \text{ ohm}$$

and $$R_2 + r_2 = 7 \text{ ohm}$$

then:

$$i_1 = (7/360)i = 20 \text{ mA}$$

and $$V \sim 120 \times 0.02 = 2.4 \text{ v} = V_{2A} \sim i_2(R_2 + r_2)$$

for a diathermy current, i, of 1A, i.e. $i_1$ is very low indeed and shows how most of the current is forced through the good plates. The patient (and also the amplifiers) are also subjected to very low potentials.

We can move up the scale of improbability and postulate that two out of the four plates short, then 3 out of the 4 plates. If we repeat the above analysis we find that the current in the faulty plates is, respectively 30 mA and 60 mA, which are still very low values.

Even if all the plates fail, we get:

$$V = i_1 jwL_1 = i_2 jwL_2 = i_3 jwL_3 = i_4 jwL_4 = \frac{120}{4} = 30 \text{ v} \quad (3.20)$$

i.e. $i_1 = i_2 = i_3 = i_4 = 0.25 \text{ A}$ which is still moderately safe.

The odds against a combination of types of fault i.e. punch-through and tear-off in such a way that all the current would go down the fault branch must also be very high. Even so, the geometries of the multi-element designs suggested in FIGS. 12, 13 and 14 must increase these odds to astronomical proportions, since they are arranged in such a way that several elements are still in contact with the skin right up to the moment of separation in accidental removal. So it can be concluded that the proposed multi-element design of neutral plate affords an extrememly high measure of patient safety.

Details (Section 2):

PHYSICAL DESIGN OF NEUTRAL PLATES

Reference is again made to the basic arrangement of compensated capacitance neutral plates shown in FIGS. 5 and 6. These basic arrangements allow both limitation of current by reactance size or limitation of current by division of the plates into elements. It can be envisaged that plates might be designed that have both these features. FIGS. 12, 13 and 14 show some suggestions for multi-element neutral plate designs.

In FIG. 12 a disc type plate is illustrated with 60 elements radiating from the centre. One arrangement could be 5 groups of 12 elements. So the 1st, 13th, 25th, 37th and 49th would be connected together, the 2nd, 14th, 26th, 38th and 50th together and so on. This design would ensure that several elements are in close contact with the skin in the tear-off type fault. The designs of FIGS. 13 and 14 are multi-element variations to suit other geometric shapes. The design of FIG. 12 would probably be best effected as an adhesive type, but could also be re-usable. The design of FIG. 13 (and of FIG. 14) is such that no adhesive is required. This would permit a re-usable type of plate, such as the cuff type illustrated. The problems would be to design the cuff such that it would be kept tight at all times without impeding the circulation and also to be conformable with all shapes of human body.

The longitudinally segmented plate of FIG. 14 can be realised in at least two forms. The bandage type illustrated is likely to be easily designed to be conformable to the human body by manufacturing it of stretchable material. It would be wrapped round a limb and clipped by means of suitable fasteners. The conformable type would be of extremely resilient material like foam plastic and could even be based on the evacuable bag principle, which allows tailoring of the device to the shape of the particular person. It could be a whole mattress under the patient and as such could include both the safety features of reactive current limitation and multi-element current sharing. These devices would be finished in flexible washable surfaces capable of being disinfected.

Details (Section 3):

A MICROPROCESSOR-CONTROLLED NEUTRAL PLATE

The drawback of a pre-operation setting up procedure, mentioned earlier to adjust amplifier gains may be eliminated by an automatically controlled system. For a single plate the arrangement of FIGS. 7 and 8 form the basis of such a control system. To do this the loop is closed such that the signal processing box (which may be integral with the amplifier) adjusts the gain of the amplifier to obtain a minimum at the input of the signal processing box. I.e. $V_2$ becomes automatically adjusted so that the quadrature term in equation (3.3) above becomes zero. $V_2$ remains proportional to the sensed current to keep in step with various settings of the diathermy power. If preset levels are reached within the control unit the diathermy would be disconnected and alarms made. This would occur if the compensation failed because:

(a) the neutral plate shorts, or
(b) the neutral plate peels off, or
(c) the reference lead peels off.

For multi-element or multiple plates there is the extra task of sharing the currents between the various branches. This might be best performed incrementally in an iterative fashion, both to prevent control interactions and interloop resonances. The aim would be to express the equations (3.17) in the real world.

Electronic logic might be used to achieve this overall control, but a more powerful solution would be a microprocessor plus an appropriate amount of memory. The microprocessor centre of the control system would accept and deliver signals under program control and by means of algorithms such that the currents in each branch would be incrementaly adjusted to achieve equality and simultaneously to minimise the potential drop between patient and diathermy unit, Vcc, on the neutral plate side. In addition, the presence of some plate punch-through faults or of a peel-of fault would be detected by internal preset limits being reached when the range of adjustment required became excessive. Alarms could be sounded or disconnection made.

The technique would be to sense the currents in each branch by the transformrs Ts1, Ts2, etc up to (in this case) Ts10. Vcc would also be sensed. These signals would be converted to a suitable digital form by the ADCs (analogue to digital convertors) and the digital processing electronics for manipulation by the microprocessor. The reverse process is achieved by further digital processing and DACs (digital to analogue convertors) to drive the transformers T1, T2 etc up to T10 such the reactive balance is achieved in each branch.

The advantages would be an easily operated, ultra-safe and rapidly adapting device giving clear signals to the operating staff. Accommodation of slight movement of the patient would also be an attractive feature.

Details (Section 4):

VARIATIONS TO SUIT CERTAIN SURGICAL OPERATING THEATRES

The background to this section is that many surgical operating theatres have special anti-static floors, the construction of which inhibits the installation of electrical services which come up through the floor. To overcome the consequential difficulties of this inhibition, three further variations of the invention are presented as follows:

(a) the concept of a multi-generator/multi-element neutral plate surgical diathermy apparatus;
(b) that the reference lead can come from a capacitive type pad; and
(c) that the concept of a full body length plate may readily extend the area of application to animals.

(Section 4.1):

THE MULTI-ELEMENT/MULTI-GENERATOR CONFIGURATION

Operation

Figure 16:
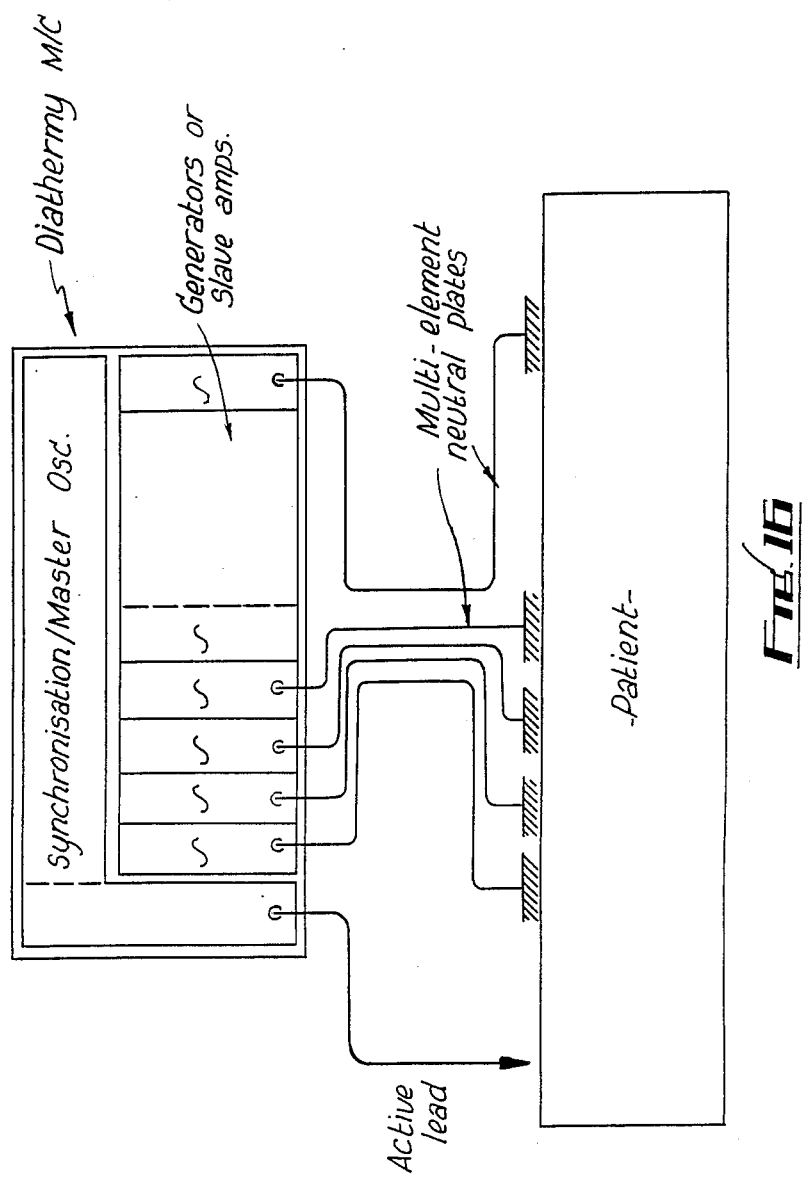
FIGS. 16, 17 and 18 illustrate three further variations of the invention.

FIG. 16 illustrates this arrangement of diathermy machine. In this set-up a separate generator is asociated with each single element of a multi-element capacitance neutral plate. It may be either a diathermy generator in its own right or an amplifier which is slaved from a master oscillator. However it is achieved, the effect would be the same, namely that the total current flow would comprise the sum of all the currents flowing through the neutral plates fromall the generators and would equal in sum the current flowing in the active lead.

Figure 17:
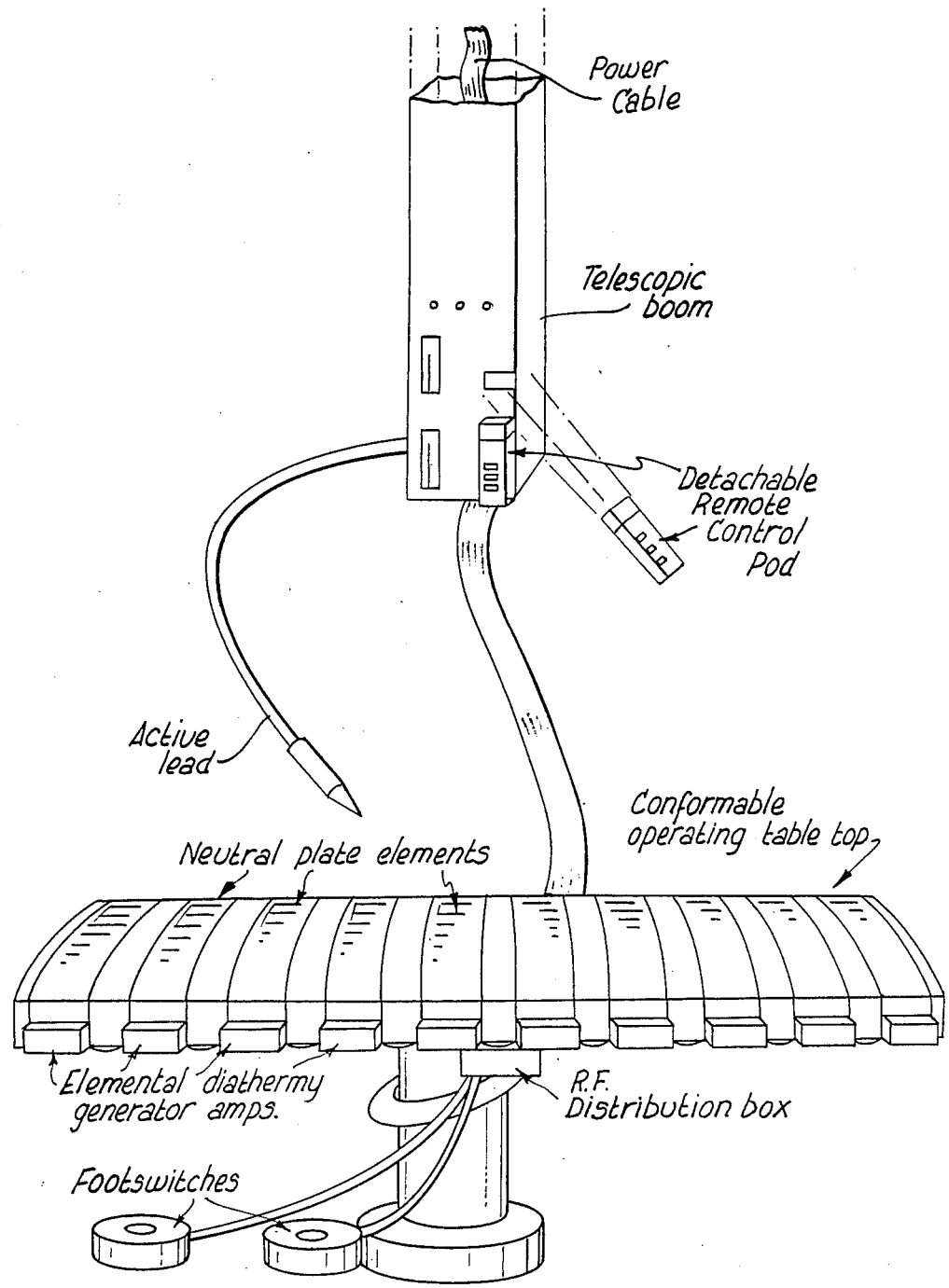

One conceptualism of this idea would be to locate these generator elements close to or, by utilising the miniaturisation of electronic components, even to integrate the generator and plate as one element. The remainder of the circuitry, e.g. logic and R.F. (radio frequency) sections could be located elsewhere. This would permit distributed solutions to the problems of implementing surgical diathermy systems in an ergonomic way. A distributed nature of the diathermy system permits installation of the plate alarm/disconnection feature. FIG. 17 illustrates one conception of this idea. Some of the circuitry is located above the operating table, while the remainder is located in a telescopic boom. Power supplies are derived from power units located remotely. In order that the boom is uncluttered by controls, these could be mounted on an infra-red signalling remote control pad similar to these used for TV and video sets. This is an advance on equipments presently employing boom extensions since the R.F. leads (active and neutral) could be kept quite short to minimise stray reactances and hence to permit the inclusion of all alarm circuits including plate voltage. The latter feature permits compaction and simplification of controls and electronic hardware.

Care would be required that the complex waveforms needed for the different diathermy modes were not distorted due to phase or timing differences between component generators. So a master oscillator is required either for the primary generation of the required waveform for subsequent amplification by matching amplifiers or for triggering the waveforms of the equivalent elemental generators.

Summing circuitry would be required to ensure that one generator did not feed directly into the output of another.

Since each generator would be provided with current limitation circuitry, the current through any individual plate element would never reach an unsafe level even with a short in or across a plate. This is an extension of the idea that by means of a large number of current branches the incidence of damaging current can be kept to a low value.

Compensation

Compensation of the capacitive reactance of the capacitive neutral plate element could be incorporated within each generator if required. However, compensation in this configuration would now only be required if the diathermy machine were earth-referred at the power output. Since modern diathermy machines are without exception non earth-referred, compensation would be unlikely to be required, the above mechanisms of current division and limitation being sufficient.

Application

One can envisage a diathermy machine which can be built up in generator modules of say 40 W output capacity each. Ten such modules would comprise a generator of capacity 400 W. This would allow a production of a basic machine with the provision of, or switching in of, varying numbers of generator/neutral plate elements. Thus the machine could be matched to different applications such as ENT (ear, nose and throat), paediatrics on to orthopaedic surgery. Possibilities open up of building up machines to accommodate all sizes of animals, as well as humans.

Control

Control might well be simplified compared with other previously described configurations. Current summing and limitation as well as alarms would be important aspects. Microprocessor-based control of all functions would allow considerable rationalisation and miniaturisation of the electronics.

Configuration and Orientation of Neutral Plate Elements

In the versions of this invention using compensation of the capacitive plate it was important to keep all the elements in roughly the same proximity to the patient so that no one branch started to draw excessive current. In this version (and indeed in compensated versions similarly controlled) since the current is limited to a safe value in any one branch the physical design of the plates is not so important. Thus the transverse pattern of plate element as depicted in FIG. 17 would be perfectly acceptable and this freedom from this constraint could allow the designer to arrive at the optimum arrangement for the plate.

Advantages

These are:

(a) Compensation not required for modern machines;

(b) Simplified control requirements;

(c) The frequency problem disappears—no electronic compensation required;

(d) A basic machine can be manufactured with modules added for various applications;

(e) The advantages of the multi-element capacitive plate are retained;

(f) Development and production costs may be significantly lower; and (g) The option of integrating elements of plate and generator together opens up the possibility of superior designs from the point of view of ergonomics.

Disadvantages

These are:

(a) The generators have to be precisely synchronised to achieve the various complex waveforms of surgical diathermy.

(b) In some countries earth-referred diathermies may still exist. These would be more easily retrofitted by means of a compensated version, which would ensure that the patient was kept at safe voltage levels.

(Section 4.2):

THE REFERENCE LEAD

Figure 18:
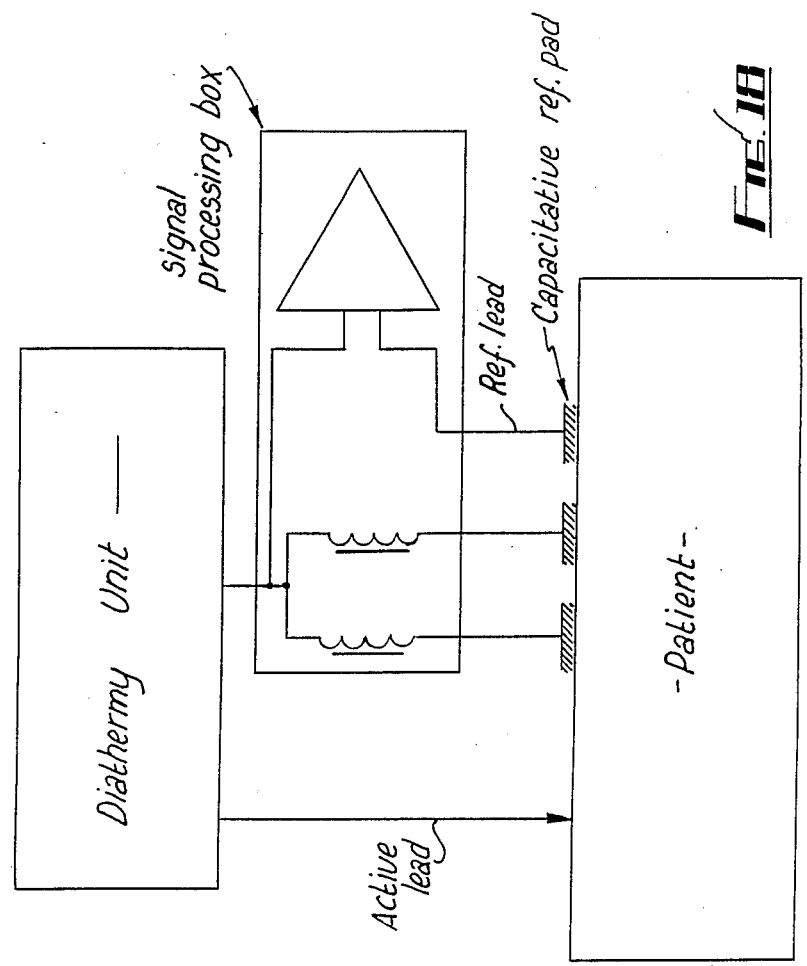
Figure 13:
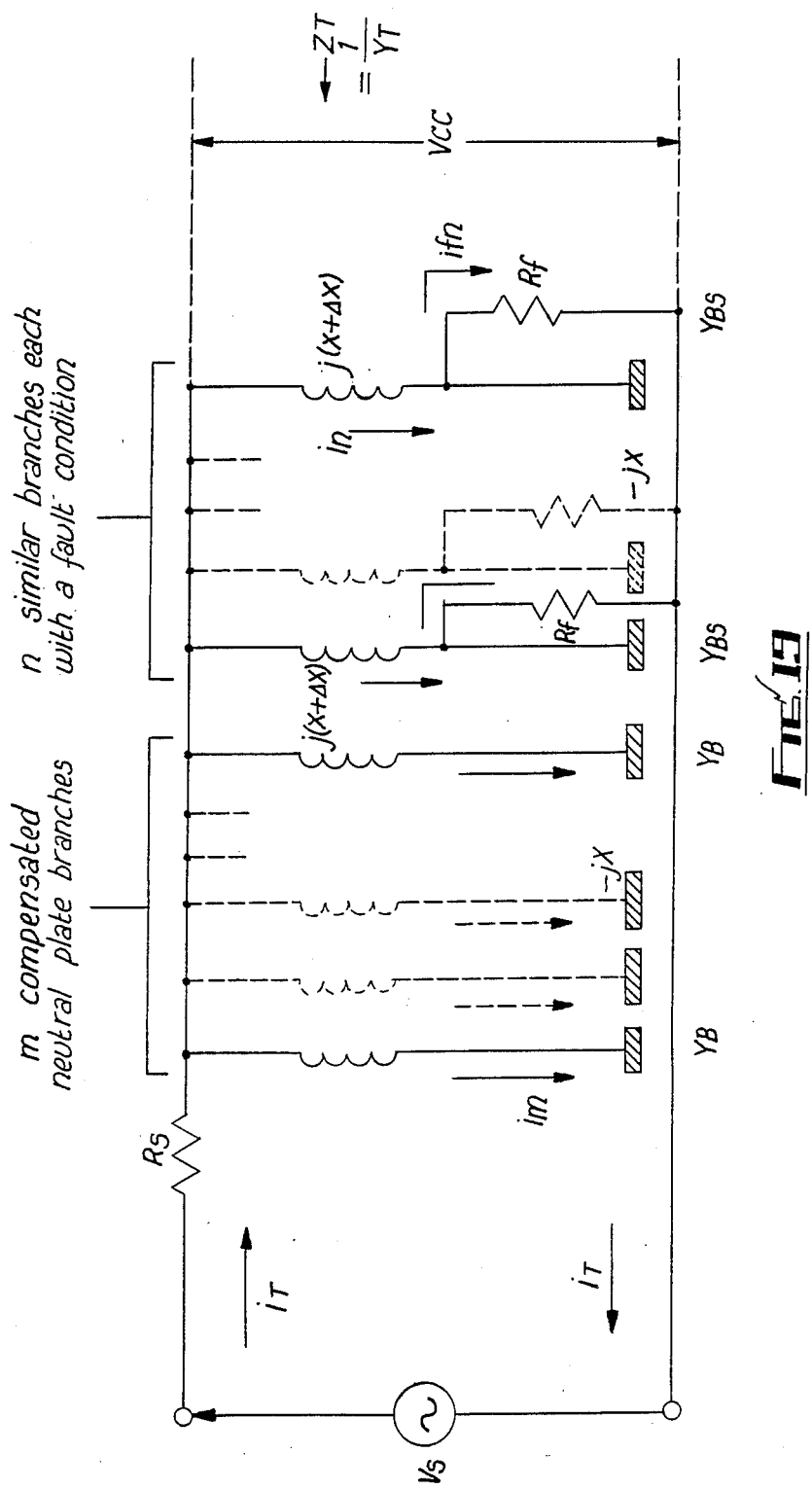

The requirement of a reference lead and pad for the purposes of supplying a reference voltage point on the patient for electronic signal processing equipment has been described above (see FIG. 7). The pad for this purpose need not be conductive as indicated, but could just as well be capacitive like the other elements of the multi-element neutral plate (see FIG. 18). The constraint would be that the reactance of the reference pad be small in relation to the input impedance of the associated signal processing equipment. The advantage is that the reference pad could be an element integral with the multi-element plate and thus simplify design and fabrication.

(Section 4.3):

SURGICAL DIATHERMY ON ANIMALS

The advantages of the full length capacitive plate (FIGS. 14 and 17) are probably also applicable in animal surgery. Since it may be that no removal of covering of hair, fur or feather would be required for the application of a neutral plate, the beast could be operated on with the minimum trauma. Indeed it might be the only way that electrical diathermy could be used with some animals. This application possibly may open up a completely new market for this invention.

Modifications and variations may be incorporated without departing from the scope of the invention.

There now follows the Appendix referred to in the description above.

APPENDIX

Analysis of Multi-Element Compensated Neutral Plate Under Fault Conditions

A1 IDENTICAL FAULT BRANCHES

FIG. 19 is the equivalent circuit of a diathermy machine connected to a patient through a compensated multi-element neutral plate. The e.m.f. of a generator is $V_s$ with a total current $i_T$. The source resistance, $R_s$, is composed of the diathermy source resistance and the body impedance of the patient. Body and cable reactance components are assumed negligible for the sake of simplicity.

The neutral plate is assumed to be composed of (m+n) elements with (m+n) compensated branches, m of which are intact and of admittance $Y_B$. There are also n elements each with a partial short depicted by identical resistance, $R_f$, across the capacitive element. The admittance of each of these branches is $Y_{BS}$. The total admittance of the neutral plate is given by:

$$Y_T = mY_B + nY_{BS} \quad (A1)$$

The potential drop across the compensated plate set is given by:

$$V_{cc} = Z_T \cdot V_s/(R_s + Z_T) \sim (Z_r/R_s) \cdot V_s = (V_s/R_s YT) = V_s/R_s(mY_B + nY_{Bs})$$

If we make the assumption that the maximum value of $i_T$ is when the maximum value of $V_s$ is $V_{smax}$, then assuming a practical value of 1 Ampere, $$i_{Tmax} = V_s/R_s = 1$$

This gives:

$$V_{ccmax} = 1/(mY_B + nY_{Bs})$$

so that the current in a fault branch is given by:

$$i_n = V_{ccmax}/Z_{Bs} = 1/Z_{Bs}(mY_B + nY_{Bs}) \quad (A2)$$

The current in a partial short, $R_n$, is given, by current division, by:

$$i_{Fn} = [(X^2 - jR_nX)/(R_n^2 + X^2)] \cdot i_n$$

The reactance of the capacitive neutral plate is $-jX$. This gives, using equation (A2):

$$i_{Fn} = (X^2 - jR_nX)/\{(R_n^2 + X^2)(mY_B + nY_{Bs})Z_{Bs}\} \quad (A3)$$

Equation (A3) can be reduced to form expressed in terms of constants a and b and the variable $R_n$. Of the following equations (A4) is the version giving the magnitude of the fault current:

$$i_{Fn} = 1/[(a+bR_n) + j(C+dR_n)] \bmod.(i_{Fn}) = [(a+bR_n)^2 + (c+dR_n)^2]^{-\frac{1}{2}} \quad (A4)$$

Values of the fault resistance can then be substituted to yield the current. The power dissipation in the fault resistance is given by:

$$P_F = i_{Fn}^2 R_n = R_n/[(a+bR_n)^2 + (c+dR_n)^2] \quad (A5)$$

The value of fault resistance which gives maximum power dissipation in the patient's flesh is found by taking the derivitive of expression (A5). So:

$$\frac{dP_F}{dR_n} = \quad (A6)$$

$$\frac{(a+bR_n)^2 + (c+dR_n)^2 - R_n[2b(a+bR_n) + 2d(c+dR_n)]}{[(a+bR_n)^2 + (c+dR_n)^2]^2}$$

The maximum value is then obtained by putting the numerator of this expression equal to zero. This gives:

$$R_n^2 = (a^2+c^2)/(b^2+d^2) \quad (A7)$$

These equations enable the plate parameters to be set to give a worst case power dissipation which is safe for the patient. For one plate element this maximum power value might be in the region of 1 Watt.

Note, however that this analysis is somewhat artificial because all the fault branches have been assumed identical. The case where one of the fault branches is different is examined below. If DX is the amount by which the inductive reactance in a branch exceeds the capacitive reactance of an element of a capacitive neutral plate then equation (A3) can be reduced to:

$$i_{Fn} = 1/\{[-R_nDX/X + jX(1+DX/X)](mY_B + nY_{Bs})\} \quad (A8)$$

(where "D" as used above and below signifies "DELTA").

This simplifies to:

$$i_{Fn} = 1/[n + m(1+X/DX) + j(m+n)R_n/X] \quad (A9)$$

and the maximum power dissipation is, from equation (A7) given by a fault resistance of:

$$R_n = [n + m(1+X/DX)]X/(m+n) \quad (A10)$$

Figure 20:
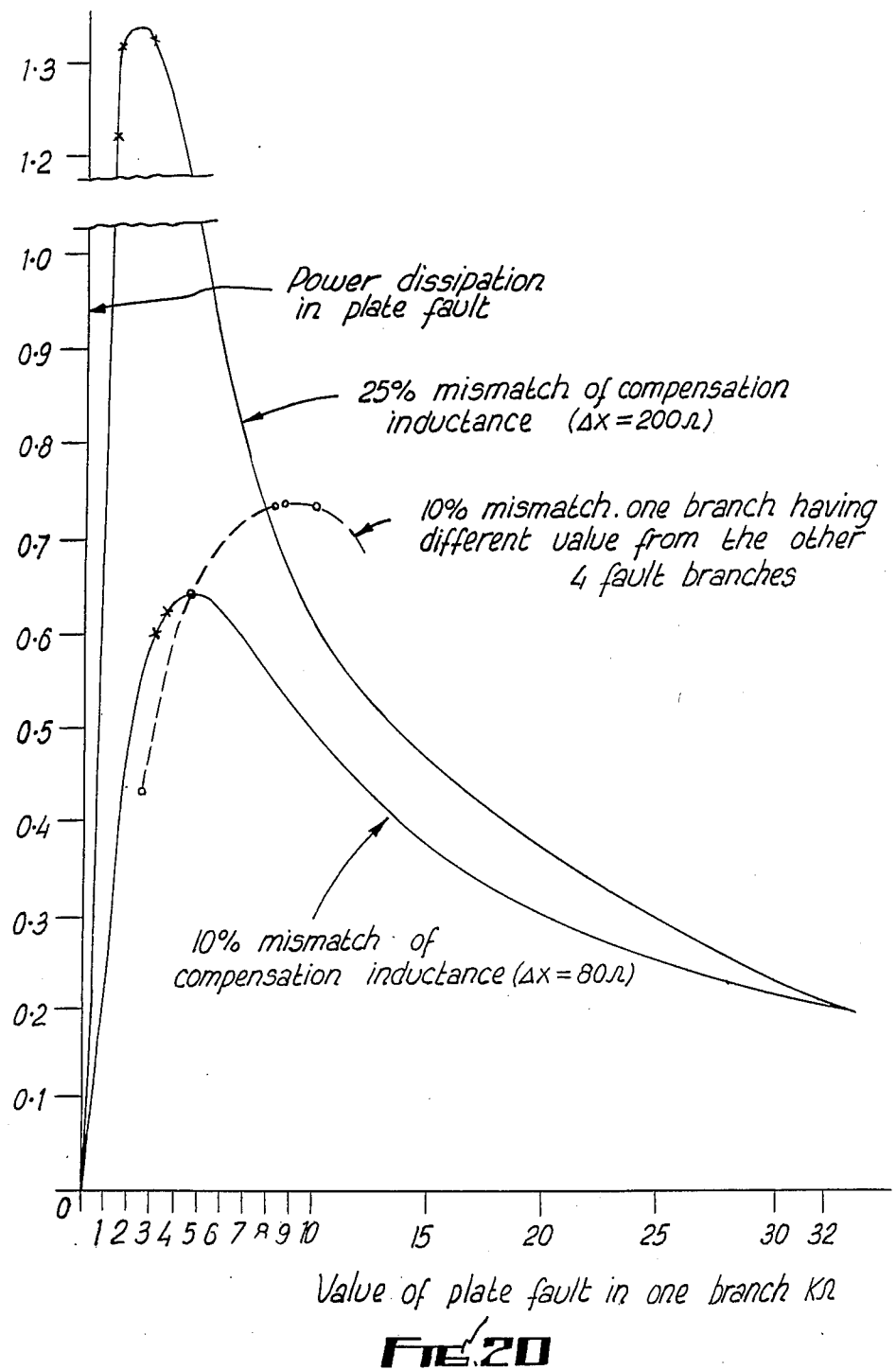
FIG. 20 is a graph illustrating power dissipation in a partial fault at maximum generator current.

So, for a 10 element neutral plate with 5 equal partial shorts (m=n=5), a reactance of X=800 ohm and a reactive tolerance of DX=80 ohm, the current, $i_{Fn}$, giving maximum power dissipation is about 11.79 mA and the power dissipation, $P_n$, is 0.667 W, which is quite modest. The power dissipation curve versus fault resistance is shown in FIG. 20, where the curve for the wider tolerance of reactive match of 25% (DX=200 ohm) is also shown. This results in a higher predicted maximum power and so leads to the conclusion that the closest matching of inductance and neutral plate capacitance reactance is desirable.

Note that perfect matching (DX=0 ohm) would give a fault current of zero for all values of fault resistance, $R_n$. As already discussed, this desirable condition may be approached by inserting a trimming capacitor in parallel with the inductor and adjusting for a mximum, current in each branch. However, the disadvantages are:

(a) some circuit complexity, (b) a setting-up procedure, and (c) the possibility of over-adjustment so that the branch goes capacitive with the danger that inter-branch resonance results in high loop currents.

We have seen that a fairly wide mismatch can be tolerated and the random values expected for the capacitive neutral plate elements might lead one to expect that at least some would closely match their compensating inductors. It would require just one neutral plate/inductor set to almost match for $mY_B$ in equation (A2) to approach infinity and therefore for $V_{cc}$ to be almost zero and hence also the fault current $i_{Fn}$. It would be prudent for correct current division for a small value power resistor to be placed in each branch. It follows also from this analysis that the division of currents among the branches depends very much on the reactance tolerance. This being so, it may be worthwhile to consider the automatic adjustment of currents in each branch to achieve even distribution. This could be done by coupling each branch into sensing circuits and then sequentially adjusting each branch by the injection of a balancing potential again via transformer. This technique would really only be viable by the use of microprocessor control to give the fast response required.

A2 EXTENSION OF PREVIOUS ANALYSIS—VARIATION OF CURRENT AND POWER IN ONE FAULT BRANCH

It is unlikely that multiple faults would exhibit in the coherent equal-valued fashion already described. We can repeat the analysis of the circuit of FIG. 19 inserting the values for the fault resistance, $R_n$, of 4800 ohm for the 10% reactance tolerance case into four of the fault branches. The fifth branch was allowed to vary and it was discovered that a new value of $R_n'$ in that branch, namely 7740 ohm, was found to give the maximum power dissipation. This last was found to be 0.742 W, somewhat higher than the previous case of all values being varied together. Other values are illustrated by the dotted curve in FIG. 20.

A3 THE WORST CASE ANALYSIS

The above-analyses may represent fairly typically what might happen in practice given that in practice the neutral plate element values will be fairly random. Nevertheless we must ask what are the most extreme conditions that could ever occur. Examination of the equation for $V_{ccmax}$ preceding equation A2 show that it is at a maximum when the branch impedances are at a maximum. Two conditions can be conceived as leading to maximum impedance in a branch:

(a) a dead short across the capacitance neutral plate so allowing the compensating inductance to be fully in play;

(b) an open circuit in the branch to given infinite impedance.

If we assume that of the 5 faulty branches 4 are in one of the above conditions then the fifth would take the highest fault current due to the high value of $V_{ccmax}$. We analyse what happens in this fifth branch.

If $Y_{Bs}'$ is the admittance of the fifth faulty branch and dashed symbols refer also to this branch then the equation for $V_{ccmax}$ may be rewritten:

$$V_{ccmax} = 1/(5Y_B + 4Y_{Bs} + Y_{Bs}') \quad (A11)$$

Equation (A2) may be rewritten $$i_n' = 1/(5Y_B Z_{Bs}' + 4Z_{Bs}'/Z_{Bs} + 1) \quad (A12)$$

and (A3)

$$i_{Fn}' = i_n(X^2 - jR_n'X)/[(R_n')^2 + X^2] \quad (A13)$$

i.e.

$$i_{Fn}' = 1/\{[-R_n'DX/X + jX(1 + DX/X)][-5j/DX - j4/(X + DX)] + 1 + jR_n'/X\} \quad (A14)$$

For condition (a):

$$i_{Fn}' = 1/(60 + j4R_n'/8800 + j6R_n'/800) \quad (A15)$$

where $DX = 80$ ohm i.e. a mismatch of 10%.
Applying equation (A7) we find:

$$R_n' = (a/d)X = 7543 \text{ ohm}$$

Also $i_{Fn}'$ is 11.785 mA and the maximum power ($P_{max}$) is 1.048 W. The figures for the case of a 25% mismatch ($DX = 200$ ohm) are:

$$R_n' = 3529 \text{ ohm}, i_{Fn}' = 23.57 \text{ mA and } P_{max} = 1.96 \text{ W}$$

For condition (b):

$$i_{Fn}' = 1/(60 + j6R_n'/800) \quad (A16)$$

for a mismatch of 10%.
The figures for this case are:

$$R_n' = 8000 \text{ ohm}, i_{Fn}' = 11.785 \text{ mA and } P_{max} = 1.111 \text{ W}$$

For the 25% mismatch case:

$$R_n' = 4000 \text{ ohm}, i_{Fn}' = 23.57 \text{ mA and } P_{max} = 2.222 \text{ W}$$

This last set of figures could be taken as the worst case figure. It is a little higher than might be comfortable for the patient, but it could be assumed to be rather unlikely or the above equations could be reworked in the light of revised design parameters. Similarly if tolerances are found to be wider than here assumed the design cycle can be repeated.

Again, but with some complexity in the electronics, automatic adjustment of the plate currents could be achieved. Simultaneous control of the plate-inductor voltage, $V_{cc}$, would achieve very high levels of patient safety indeed.

We claim:

1. Surgical diathermy apparatus comprising a power source, an active electrode for operation on a patient, at least one circuit means for attachment to the patient, interconnection means operatively interconnecting said power source with said active electrode and said at least one circuit means, each said circuit means comprising a respective capacitive neutral plate for attachment to the patient, a respective transformer interconnecting said power source to said respective capacitive neutral plate, and a respective potential compensator comprising a respective amplifier transformer-coupled by said respective transformer in series between said power source and said respective capacitive neutral plate, said respective amplifier being operated to inject a voltage through the respective transformer which is substantially equal to the potential drop across the capacitive reactance of the respective capacitive neutral plate.

2. Surgical diathermy apparatus as claimed in claim 1 wherein each said circuit means includes a compensation potential level adjuster operatively coupled to the respective potential compensator to adjust the level of the compensation potential provided by the respective potential compensator.

3. Surgical diathermy apparatus as claimed in claim 1 wherein each said circuit means includes an open circuit fault condition detector operatively coupled to detect open circuit fault conditions of the respective capacitive neutral plate.

4. Surgical diathermy apparatus as claimed in claim 1 wherein each said circuit means includes a short circuit fault condition detector operatively coupled to detect short circuit fault conditions of the respective capacitive neutral plate.

5. Surgical diathermy apparatus as claimed in claim 1 wherein each said circuit means includes a respective open circuit fault condition detector and a respective short circuit fault condition detector operatively coupled respectively to detect open circuit fault conditions and short circuit fault conditions of the respective capacitive neutral plate, a respective alarm system operatively associated with the respective fault condition detectors to give an alarm upon detection of a fault condition, and respective deactivation means operatively coupled to deactivate the diathermy apparatus upon detection of a fault condition.

6. Surgical diathermy apparatus as claimed in claim 1 including a plurality of compensated capacitive neutral plates which are operatively coupled in circuit to provide an automatic reduction of current in a faulty plate.

7. Surgical diathermy apparatus as claimed in claim 1 wherein said circuit means includes an array of neutral capacative plates which are operatively coupled in circuit such that the statistical probability of a significant fault current occurring is minimised.

8. Surgical diathermy apparatus as claimed in claim 1 including an automatic control circuit operatively coupled to monitor the voltages and currents from the power source and to automatically control each potential compensator.

9. Surgical diathermy apparatus as claimed in claim 1 wherein said power source comprises a respective diathermy power generator operatively coupled to each said circuit means, and means linking each said power generator for mutually synchronous operation.

10. Surgical diathermy apparatus as claimed in claim 1 wherein said power source comprises a respective diathermy power amplifier operatively coupled to each said circuit means, and a master oscillator operatively coupled to each said power amplifier to drive each said power amplifier in mutually synchronous operation.

* * * * *